(12) United States Patent
Wang et al.

(10) Patent No.: US 12,349,997 B2
(45) Date of Patent: Jul. 8, 2025

(54) SURGICAL INSTRUMENT, SLAVE OPERATING DEVICE, AND SURGICAL ROBOT

(71) Applicant: Shenzhen Edge Medical CO., Ltd., Guangdong (CN)

(72) Inventors: Jianchen Wang, Shenzhen (CN); Zhongbing Wu, Shenzhen (CN)

(73) Assignee: Shenzhen Edge Medical CO., Ltd., Guangdong (CN)

(*) Notice: Subject to any disclaimer, the term of this patent is extended or adjusted under 35 U.S.C. 154(b) by 258 days.

(21) Appl. No.: 18/029,629

(22) PCT Filed: Dec. 4, 2020

(86) PCT No.: PCT/CN2020/133722
§ 371 (c)(1),
(2) Date: Mar. 30, 2023

(87) PCT Pub. No.: WO2022/068039
PCT Pub. Date: Apr. 7, 2022

(65) Prior Publication Data
US 2023/0372041 A1 Nov. 23, 2023

(30) Foreign Application Priority Data

Sep. 30, 2020 (CN) .......................... 202011066539.9
Sep. 30, 2020 (CN) .......................... 202011066540.1

(51) Int. Cl.
*A61B 34/37* (2016.01)
*A61B 17/29* (2006.01)
(Continued)

(52) U.S. Cl.
CPC .............. *A61B 34/37* (2016.02); *A61B 17/29* (2013.01); *A61B 34/71* (2016.02); *A61B 34/74* (2016.02); *A61B 2034/305* (2016.02)

(58) Field of Classification Search
CPC ......... A61B 34/37; A61B 34/71; A61B 34/74; A61B 17/29; A61B 2034/305
See application file for complete search history.

(56) References Cited

U.S. PATENT DOCUMENTS 6,394,998 B1 * 5/2002 Wallace ................. A61B 34/35
901/29
6,840,938 B1 * 1/2005 Morley ................. A61B 34/71
901/29

(Continued)

FOREIGN PATENT DOCUMENTS

EP 2313018 B1 3/2012

*Primary Examiner* — Zakaria Elahmadi
(74) *Attorney, Agent, or Firm* — ScienBiziP, P.C.

(57) ABSTRACT

A surgical instrument, a slave operation device using the surgical instrument, and a surgical robot which has the slave operation device. The surgical instrument includes an end effector, a first pair of cables, and a second pair of cables, a distal end of the first pair of cables is arranged at an executive component of the end effector, and said pair of cables is used for manipulating the yaw movement of the end effector, a distal end of the second pair of cables is arranged on a second frame, a proximal end of the second pair of cables is connected to a drive apparatus and same is used for manipulating the pitch of the end effector, and pulleys guiding the first pair of cables and the second pair of cables are arranged on a first frame.

19 Claims, 18 Drawing Sheets

(51) Int. Cl.
*A61B 34/00* (2016.01)
*A61B 34/30* (2016.01)

(56) References Cited

U.S. PATENT DOCUMENTS

| | | | |
|---|---|---|---|
| 2008/0046122 A1* | 2/2008 | Manzo | A61B 90/98 700/245 |
| 2011/0071544 A1* | 3/2011 | Steger | A61B 17/3498 606/130 |
| 2017/0165009 A1* | 6/2017 | Chaplin | B25J 9/1045 |
| 2017/0165016 A1* | 6/2017 | Chaplin | A61B 34/71 |
| 2019/0328467 A1 | 10/2019 | Waterbury et al. | |
| 2020/0054408 A1 | 2/2020 | Schuh et al. | |

* cited by examiner

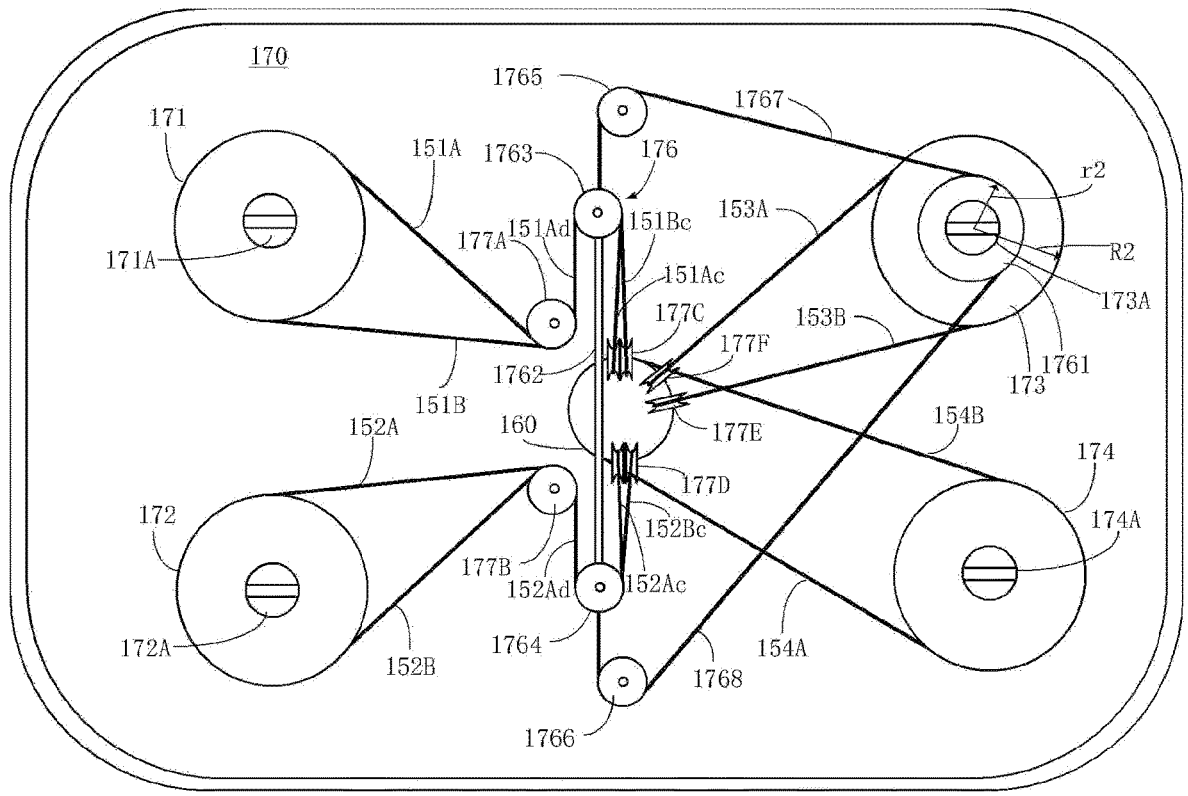
FIG. 9A
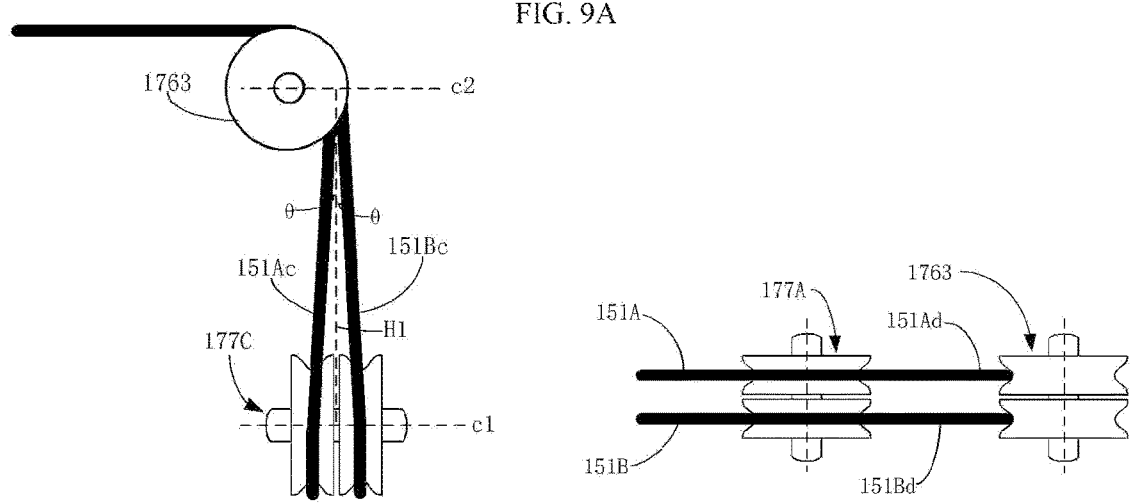
FIG. 9B
FIG. 9C

SURGICAL INSTRUMENT, SLAVE OPERATING DEVICE, AND SURGICAL ROBOT

FIELD

The subject matter herein generally relates to medical instrument, in particular to a surgical instrument, a slave operation device having the surgical instrument, and a surgical robot having the slave operation device.

BACKGROUND

Minimally invasive surgery refers to a surgical method of performing a procedure in a human body cavity using modern medical instruments such as laparoscopes, thoracoscopes, and so on. Compared with traditional surgery methods, minimally invasive surgeries are characterized by small trauma and low pain level to the patients, fast recovery, and the like.

With advances in science and technology, minimally invasive surgical robot technologies are becoming more sophisticated and widely used. A typical minimally invasive surgical robot includes a main operation console and a slave operation device, the main operation console is configured to send a control command to the slave operation device according to a doctor's operations to control the slave operation device, and the slave operation device is configured to respond to a control command of the main operation console, and performing corresponding surgical operations.

The slave operation device usually includes a surgical instrument which are detachable to the slave operation device, the surgical instrument includes a driving apparatus and an end effector. The end effector is configured to perform the surgical operations, the driving apparatus is configured to connect the surgical instrument to the slave operation device, and drives the end effector to move by the driving power from the slave operation device. The driving apparatus is connected to the end effector through driving cables, and the driving apparatus manipulates the end effector to move through the driving cables. The end effector generally comprises a first U-shaped frame and a second U-shaped frame. In related art, each of the two U-shaped frames is provided with a pair of pulleys for guiding the driving cable, wherein the first U-shaped frame is fixed, and the second U-shaped frame might rotate around the first U-shaped frame to perform a pitch movement of the end effector, so that one pulley on the second U-shaped frame rotates around the first U-shaped frame together with the second U-shaped frame, and one end of the pulley shaft of one pair of pulleys on the second U-shaped frame is in the air. In such a construction, the pulley on the second U-shaped frame may easily fall off which are potential safety hazards. Furthermore, the volume of the end effector is relatively large. In addition, a winding manner of two driving cables on the end effectors is crossed, wherein the driving cables are used for driving the end effector to open or close and/or pitch, the winding manner of two driving cables is complex, and assembling the two driving cables may be difficult.

SUMMARY

Based on this, in order to solve the above problems, the present disclosure provides a surgical instrument, a slave operation device having the surgical instrument, and a surgical robot having the slave operation device, wherein the surgical instrument comprises:

an end effector, comprising a first frame, a second frame, and an executive component, the second frame being rotatably connected to the first frame, and the executive component being rotatably connected to the second frame;

a driving cable, comprising a first pair of cables and a second pair of cables, a distal end of the first pair of cables being arranged at the executive component, a distal end of the second pair of cables being arranged on the second frame, a first pair of pulleys and a second pair of pulleys for guiding the first pair of cables and the second pair of cables being arranged on the first frame, and the second pair of pulleys being disposed between the first pair of pulleys and the executive component; and a driving apparatus, configured to drive the executive component to rotate relative to the second frame through the first pair of cables whereby the end effector performs a yaw movement, and further configured to drive the second frame to rotate relative to the first frame through the second pair of cables whereby the end effector performs a pitch movement.

In one embodiment, the first pair of cables comprises a first driving cable and a second driving cable, each of the first driving cable and the second driving cable is connected to one side of the executive component; the driving apparatus causes the end effector to perform the yaw movement by pulling one of the first driving cable and the second driving cable, and releasing the other one of the first driving cable and the second driving cable.

In one embodiment, the second pair of cables is located between the first driving cable and the second driving cable.

In one embodiment, the second pair of cables comprises a third driving cable and a fourth driving cable, each of the third driving cable and the fourth driving cable is connected to one side of the second frame; the driving apparatus causes the end effector to perform the pitch movement by pulling one of the third driving cable and the fourth driving cable, and releasing the other one of the third driving cable and the fourth driving cable.

In one embodiment, a winding manner of the first driving cable around the first pair of pulleys and the second pair of pulleys is the same as that of the second driving cable around the first pair of pulleys and the second pair of pulleys.

In one embodiment, the first pair of pulleys comprises a first pulley and a second pulley connected in sequence to a shaft, the second pair of pulleys comprises a third pulley and a fourth pulley that are connected in sequence to another shaft, a part of the first driving cable in contact with the third pulley is between a part of the first driving cable in contact with the first pulley and with the executive component; a part of the second driving cable in contact with the fourth pulley is between a part of the second driving cable in contact with the second pulley and with the executive component.

In one embodiment, a part between the first pair of pulleys and the first frame is located on a side of the second pair of pulleys same as a side where the fourth driving cable is located.

In one embodiment, the driving apparatus releases the third driving cable and pulls the fourth driving cable so as to increase a wrapping length of the first driving cable on the first pulley and a wrapping length of the second driving cable on the second pulley simultaneously, whereby the second frame rotates relative to the first frame.

In one embodiment, the driving apparatus comprises a driving unit and a decoupling member, one end of the second pair of cables is connected to the driving unit, the driving unit drives the end effector to perform the pitch movement through the second pair of cables;

the decoupling member comprises a main decoupling element and a slave decoupling element, the main decoupling element and the slave decoupling element are arranged coaxially, the main decoupling element is configured for coaxially rotating with the driving unit and driving the slave decoupling element to move so as to increase or reduce a length of the first pair of cables in the driving apparatus, so that the driving unit drives the end effector to perform the pitch movement.

In one embodiment, the main decoupling element drives the slave decoupling element to move linearly to increase or decrease the length of the first pair of cables in the driving apparatus.

In one embodiment, the first pair of cables comprises a first driving cable and a second driving cable, the first driving cable and the second driving cable cooperatively drive the end effector to perform the yaw movement, the driving unit rotates and pulls one of the third driving cable and fourth driving cable, and releases the other one cable such that lengths of the first driving cable and the second driving cable on the end effector increase or decrease simultaneously.

In one embodiment, the driving unit and the main decoupling element are configured to rotate in a first direction, the driving unit releases the third driving cable and pulls the fourth driving cable to increase the lengths of the first driving cable and the second driving cable on the end effector, and the slave decoupling element moves when driven by the main decoupling element to reduce the lengths of the first driving cable and the second driving cable in the driving apparatus.

In one embodiment, the driving unit and the main decoupling element are configured to rotate in a second direction opposite to the first direction, the driving unit pulls the third driving cable and releases the fourth driving cable, so that the lengths of the first driving cable and the second driving cable on the end effector are reduced, and the lengths of the first driving cable and the second driving cable in the driving apparatus are increased simultaneously.

In one embodiment, the slave decoupling element comprises a carriage and a guiding portion, the guiding portion is mounted at one end of the carriage, the first pair of cables extends to the end effector after the first pair of cables is guided by the guiding portion, and the main decoupling element is connected to the carriage and drives the carriage to move so as to change the length of the first pair of cables in the driving apparatus.

In one embodiment, the slave decoupling element further comprises a first decoupling cable and a second decoupling cable, the main decoupling element is connected with the carriage through the first decoupling cable and the second decoupling cable, and the main decoupling element is configured for driving the carriage to move through the first decoupling cable and the second decoupling cable so as to change the length of the first pair of cables in the driving apparatus.

In one embodiment, the main decoupling element rotates in the first direction to release the first decoupling cable and pull the second decoupling cable such that the carriage moves in a direction for reducing the lengths of the first driving cable and the second driving cable in the driving apparatus.

In one embodiment, the main decoupling element rotates in the second direction opposite to the first direction to pull the first decoupling cable and release the second decoupling cable such that the carriage moves in a direction reducing the lengths of the first driving cable and the second driving cable in the driving apparatus.

In one embodiment, the driving apparatus further comprises a first guiding pulley, the first pair of cables extends to the end effector, a part of the first pair of cables in contact with the guiding portion is between a part of the first pair of cables in contact with the first guiding pulley and with the end effector, and a moving direction of the carriage is parallel to a portion of the first pair of cables between the first guiding pulley and the guiding portion.

In one embodiment, a proximal end of the second frame has an annular groove configured for guiding and accommodating the second pair of cables.

In one embodiment, both a radius of the first pulley and a radius of the second pulley is r1, a radius of the main decoupling element is r2, a radius of the driving unit is R2, a radius of the annular groove is R1, and the r1, r2, R1, and R2 satisfy the following relationship:

$$\frac{R2}{r2} = 2*N\frac{R1}{r1}$$

wherein, N is a number of the guiding portion.

In one embodiment, the N is equal to 1.

In one embodiment, a length variation of the first driving cable in the driving apparatus is twice as much as a moving distance of the slave decoupling element.

In one embodiment, a movement speed of the carriage is proportional to a rotational linear speed of the main decoupling element.

In one embodiment, a rate of length change of the first pair of cables in the driving apparatus is proportional to a linear motion speed of the carriage.

In one embodiment, the first frame has a first hole and a second hole, the first hole is configured for the first driving cable to pass through, the second hole is configured for the second driving cable to pass through, the first hole and the second hole are located on a same side of a plane containing an axis defined by the first pair of pulleys and an axis defined by the second pair of pulleys.

In one embodiment, the executive component further comprises a first insulation member, a second insulation member, a third insulation member, and an electric cable for supplying power to the executive component, a proximal end of the executive component is connected to a distal end of the electric cable in the first insulation member, the second insulation member is connected to a distal end of the first insulation member, an end portion of the executive component is fixed in the second insulation member, and the distal end of the electric cable is accommodated in the third insulation member and extends into the first insulation member to be connected to a proximal end of the executive component.

In one embodiment, the second pulley and the fourth pulley have a guiding portion configured for guiding the electric cable.

A slave operation device, comprising a robotic arm and a surgical instrument, the surgical instrument being mounted on the robotic arm, and the robotic arm being configured for manipulating the surgical instrument to move, the surgical instrument comprising:

an end effector, comprising a first frame, a second frame, and an executive component, the second frame being rotatably connected to the first frame, and the executive component being rotatably connected to the second frame;

a driving cable, comprising a first pair of cables and a second pair of cables, a distal end of the first pair of cables being arranged at the executive component, a distal end of the second pair of cables being arranged on the second frame, a first pair of pulleys and a second pair of pulleys for guiding the first pair of cables and the second pair of cables being arranged on the first frame, and the second pair of pulleys being disposed between the first pair of pulleys and the executive component; and a driving apparatus, configured to drive the executive component to rotate relative to the second frame through the first pair of cables whereby the end effector performs a yaw movement, and further configured to drive the second frame to rotate relative to the first frame through the second pair of cables whereby the end effector performs a pitch movement.

A surgical robot, comprising a main operation console and a slave operation device, the slave operation device performing a corresponding operation according to an instruction from the main operation console, the slave operation device comprising a robotic arm and a surgical instrument, the surgical instrument being mounted on the robotic arm, and the robotic arm being configured for manipulating the surgical instrument to move, the surgical instrument comprising:

an end effector, comprising a first frame, a second frame, and an executive component, the second frame being rotatably connected to the first frame, and the executive component being rotatably connected to the second frame;

a driving cable, comprising a first pair of cables and a second pair of cables, a distal end of the first pair of cables being arranged at the executive component, a distal end of the second pair of cables being arranged on the second frame, a first pair of pulleys and a second pair of pulleys for guiding the first pair of cables and the second pair of cables being arranged on the first frame, and the second pair of pulleys being disposed between the first pair of pulleys and the executive component; and a driving apparatus, configured to drive the executive component to rotate relative to the second frame through the first pair of cables whereby the end effector performs a yaw movement, and further configured to drive the second frame to rotate relative to the first frame through the second pair of cables whereby the end effector performs a pitch movement.

Since two pairs of pulleys of the end effector of the surgical instrument are fixed to the same frame without the pulley shaft being empty, there is no risk of the pulleys falling off, making the end effector of the present disclosure safer and has a smaller volume. The two driving cables for opening and closing and/or pitching and yawing are wound symmetrically side by side on the end effector, making assembly easier and the overall size of the end effector smaller than cross-winding manner.

BRIEF DESCRIPTION OF THE DRAWINGS

FIG. 9A is a schematic view of a driving apparatus according to an embodiment.

FIGS. 9B and 9C are partial schematic views of the first driving cable and the second driving cable in the driving apparatus shown in FIG. 9A around a guiding pulley.

DETAILED DESCRIPTION

Figure 1:
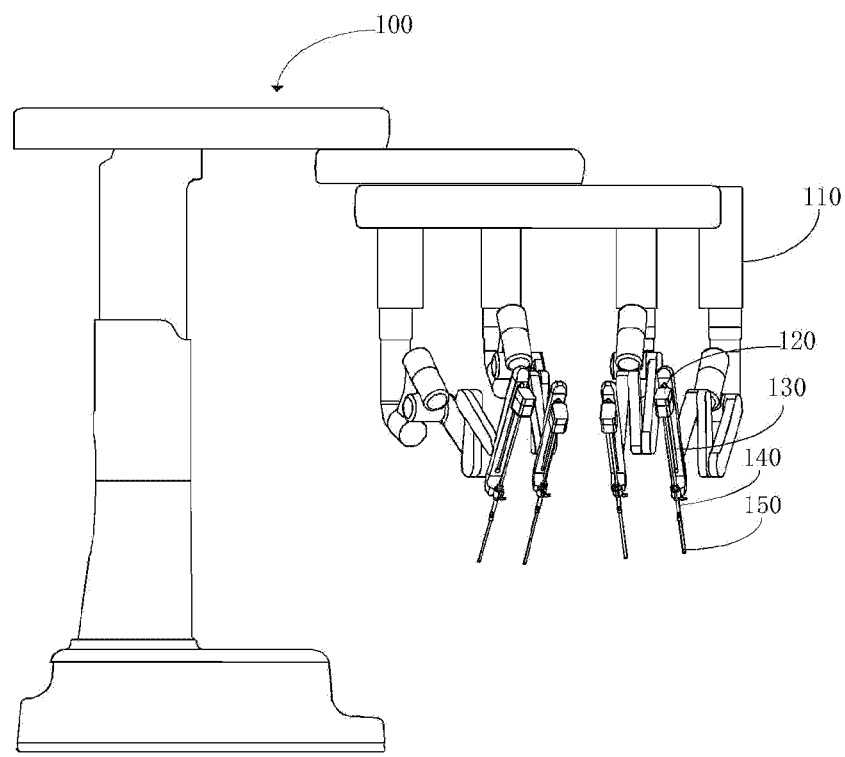
FIG. 1 is a schematic structural view of a slave operation device of a surgical robot according to an embodiment.

In order to facilitate understanding of the present disclosure, the present disclosure will be described more fully hereinafter with reference to the accompanying drawings. Preferred embodiments of the present disclosure are given in the drawings. However, the present disclosure may be implemented in many different forms and is not limited to the embodiments described herein. On the contrary, the purpose of providing these embodiments is to make a more thorough and comprehensive understanding of the present disclosure.

It should be noted that when a member is referred to as being "disposed on" another member, it may be directly on the other member or intervening members may also be present. When a member is considered to be "connected" to another member, it may be directly connected to another member or intervening members may be present at the same time. When a member is considered to be "coupled" to another member, it may be directly coupled to another member or intervening members may be present at the same time. As used herein, the terms "vertical", "horizontal", "left", "right" and the like are intended for purposes of illustration only and are not intended to be limiting. As used herein, the terms "distal end" and "proximal end" are common terms in the art of interventional medical devices, where "distal end" refers to the end far away from the operator during the surgical procedure, and the "proximal end" refers to the end close to the operator during the surgical procedure.

Unless defined otherwise, all technical and scientific terms used herein have the same meaning as commonly understood by one of ordinary skill in the art. The terminology used herein is for the purpose of describing particular embodiments only and is not intended to be limiting of the invention. As used herein, the term "and/or" includes all combinations of one or more of the associated listed items.

Figure 2:
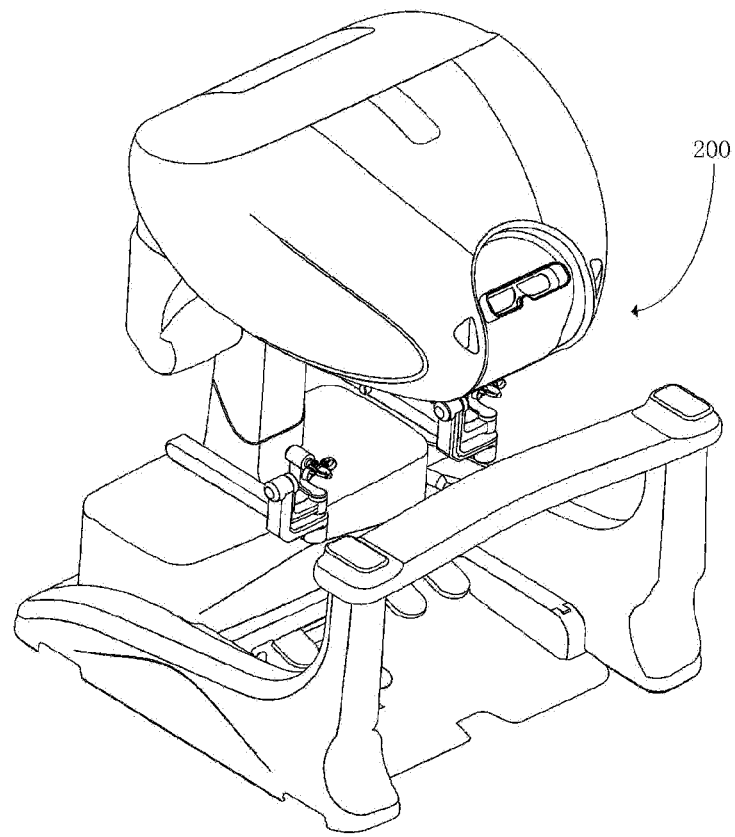
FIG. 2 is a schematic structural view of a main operation console of a surgical robot according to an embodiment.

A minimally invasive surgical robot generally includes a slave operation device and a main operation console. A slave operation device 100 of an example of present disclosure as shown in FIG. 1, a main operation console 200 of an example of present disclosure as shown in FIG. 2, a surgeon controls the slave operation device 100 by using the main operation console 200, the slave operation device 100 performs surgery according to commands sent by the main operation console 200. The main operation console 200 and the slave operation device 100 may be placed in an operating room or may be placed in different rooms, the main operation console 200 and the slave operation device 100 may be distanced remotely, for example, the main operation console 200 and the slave operation device 100 are located in different cities. The main operation console 200 and the slave operation device 100 transmit data mutually by wire or wireless, for example, the main operation console 200 and the slave operation device 100 transmit data mutually by wire when both of the main operation console 200 and the slave operation device 100 located in an operating room, the main operation console 200 and the slave operation device 100 transmit data mutually by 5G wireless data transmission.

Figure 3:
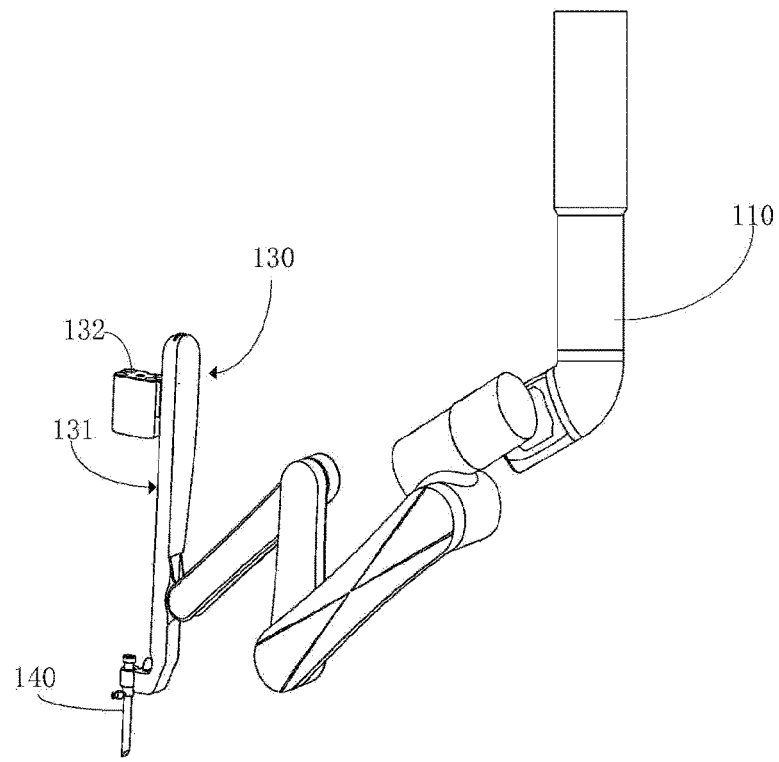
FIG. 3 is a schematic structural view of a robotic arm of a slave operation device according to an embodiment.

As shown in FIG. 1, the operating device 100 includes a plurality of robotic arms 110, each of the robotic arms 100 includes a plurality of joints and an instrument holder 130, the plurality of joints are linked to effect multiple degrees of freedom of motion of the instrument holder 130, a surgical instrument 120 is mounted on the instrument holder 130, the instrument 120 is extending to a human body via a cannula 140 fixed on the distal of the instrument holder 130. The robotic arms 110 are configured to drive the surgical instrument 120 to perform the surgery. The surgical instrument 120 is detachably mounted on the instrument holder 130, such that different types of surgical instruments 120 can be changed at any time or removed to rinse or disinfect the surgical instruments 120. As shown in FIG. 3, the instrument holder 130 includes an instrument holding body 131 and an instrument mounting frame 132, the instrument mounting frame 132 is configured to mount the surgical instrument 120, the instrument mounting frame 132 may be sliding on the instrument holding body 131 so as to drive the surgical instrument 120 to insert or retract along the instrument body 131.

Figure 4:
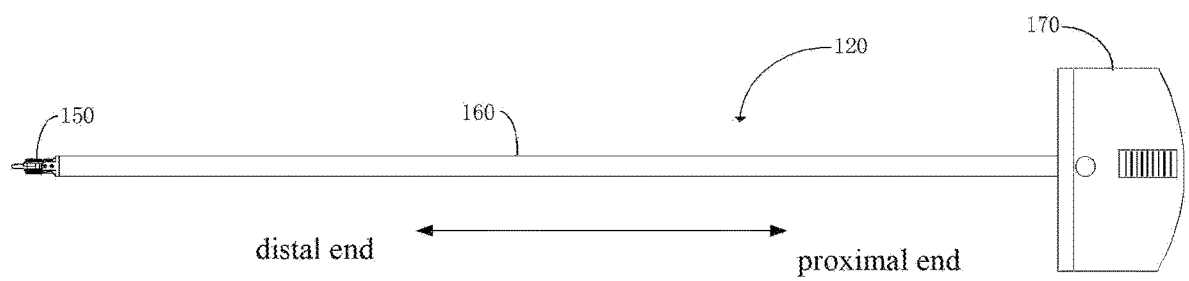
FIG. 4 is a schematic structural view of a surgical instrument according to an embodiment.

As shown in FIG. 4, the surgical instrument 120 includes a driving apparatus 170 located on proximal end of the surgical instrument 120, an end effector 150 located on the distal end of the surgical instrument 120, and an elongated shaft 160 between the driving apparatus 170 and the end effector 150. The driving apparatus 170 is configured to connect to the instrument mounting frame 132 of the instrument holder 130, the instrument mounting frame 132 has a plurality of actuators (not shown), the plurality of actuators are coupled with the driving apparatus 170 so as to transfer driving power from the actuators to the driving apparatus 170. The elongated shaft 160 is used for connecting the driving apparatus 170 and the end effector 150, the elongated shaft 160 is hollow for driving cables to pass through, the driving apparatus 170 drives the end effector 150 to move by the driving cables, such that the end effector 150 performs a related surgery operation.

Figure 5A:
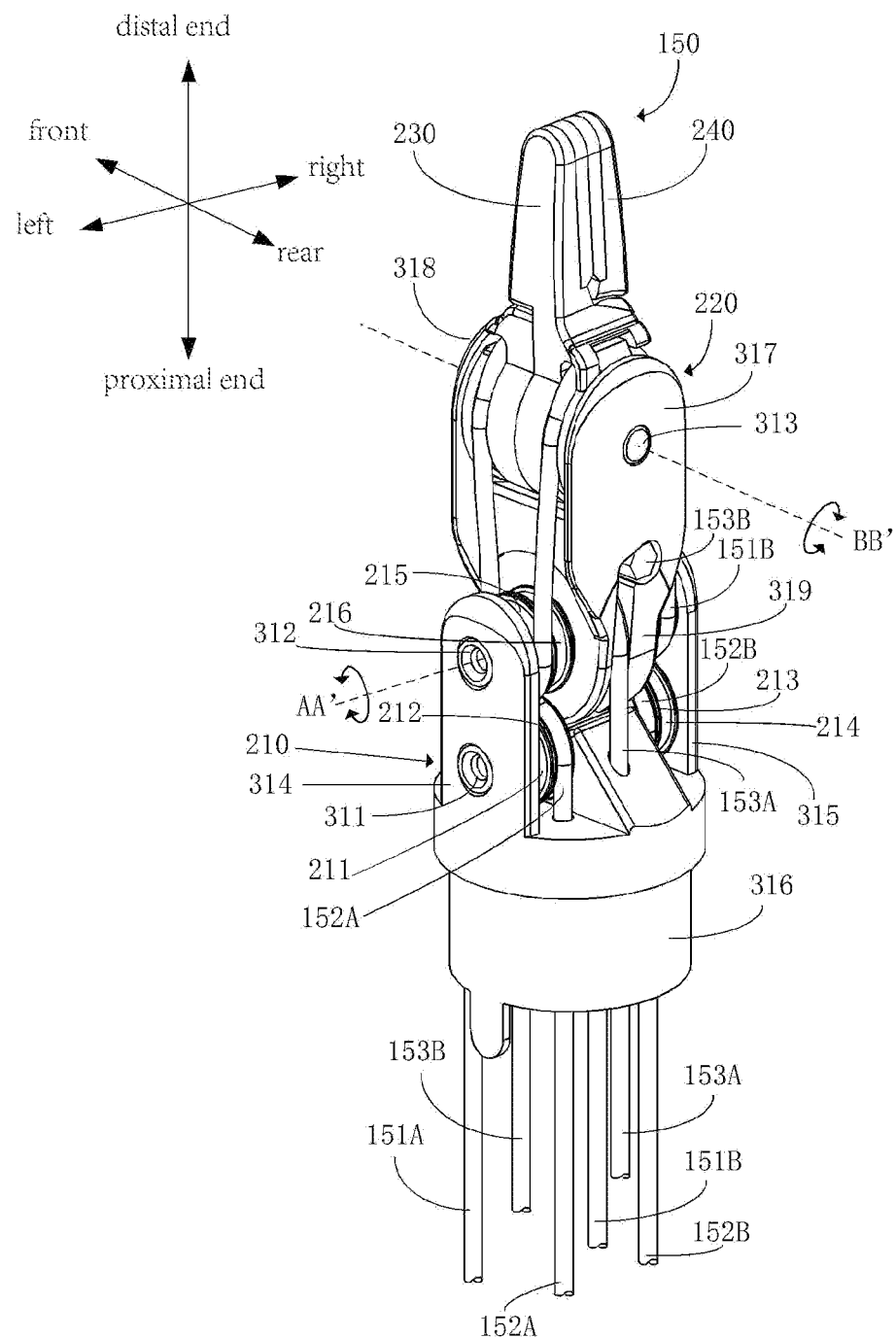
FIGS. 5A, 5B, 5C and 5D are schematic structural views of end effector according to an embodiment.

FIGS. 5A-5D are schematic structural views of end effector 150 according to an embodiment of the present disclosure. As shown in FIG. 5A, the end effector 150 includes a first support member 210 and a second frame member 220, a distal end of the first support member 210 includes a first pillar 314 and a second pillar 315, a proximal end of the first support member 210 includes a chassis 316, an end of the chassis 316 is connected to the elongated shaft 160. The first pillar 314 and the second pillar 315 are extending from the other end of the chassis 316 toward the distal end of the end effector 150, such that the first pillar 314, the second pillar 315 and the chassis 316 form a clevis.

A first pin 311 and a second pin 312 are disposed between the first pillar 314 and the second pillar 315, an end of the first pin 311 is fixed to the first pillar 314, the other end of the first pin 311 is fixed to the second pillar 315, similarly, an end of the second pin 312 is fixed to the first pillar 314, the other end of the second pin 312 is fixed to the second pillar 315. The first pin 311 and the second pin 312 are disposed side by side on the first pillar 314 and the second pillar 315, wherein the first pin 311 is closer to the chassis 316 of the first support member 210 than the second pin 312.

Figure 5B:
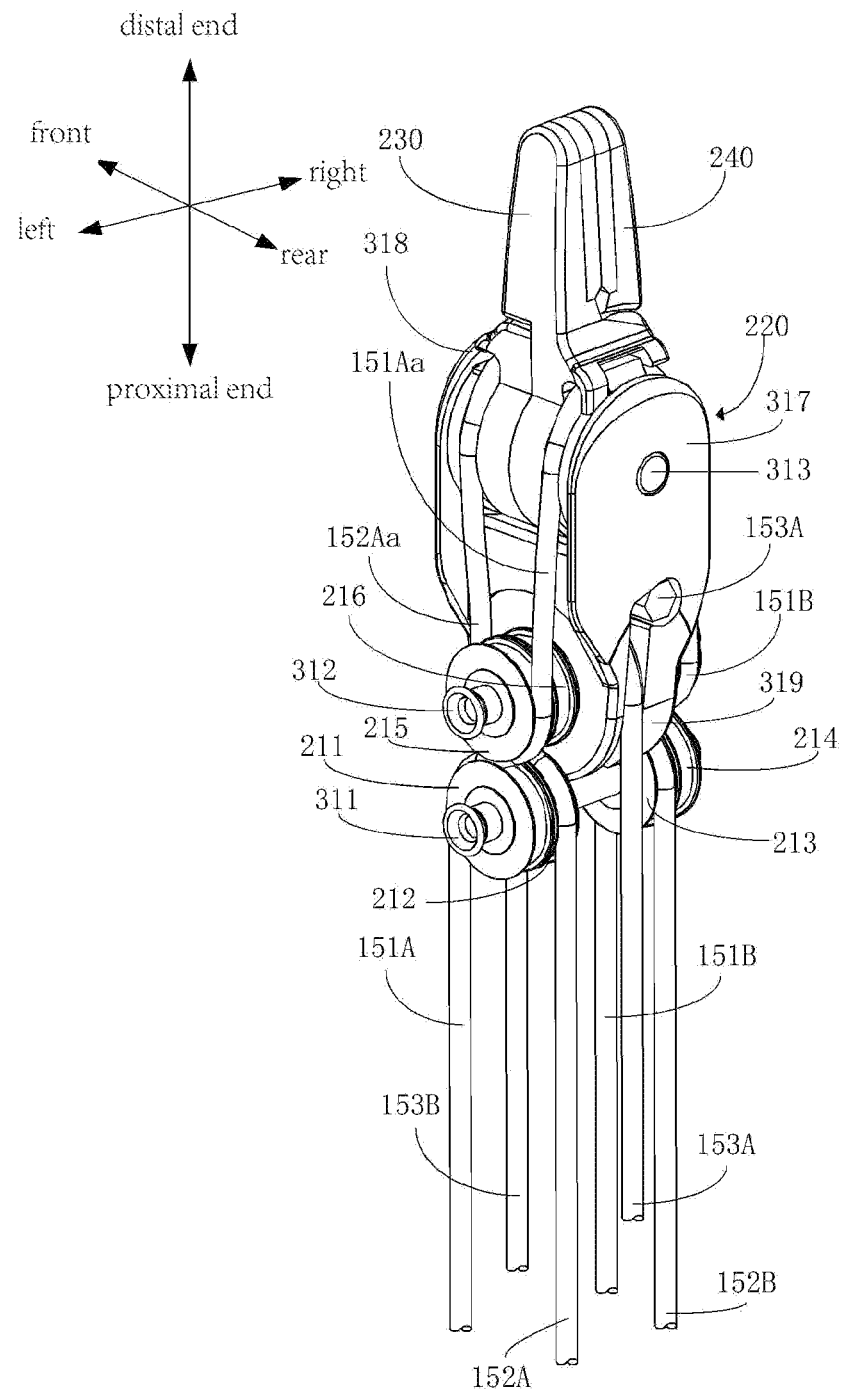
Figure 5C:
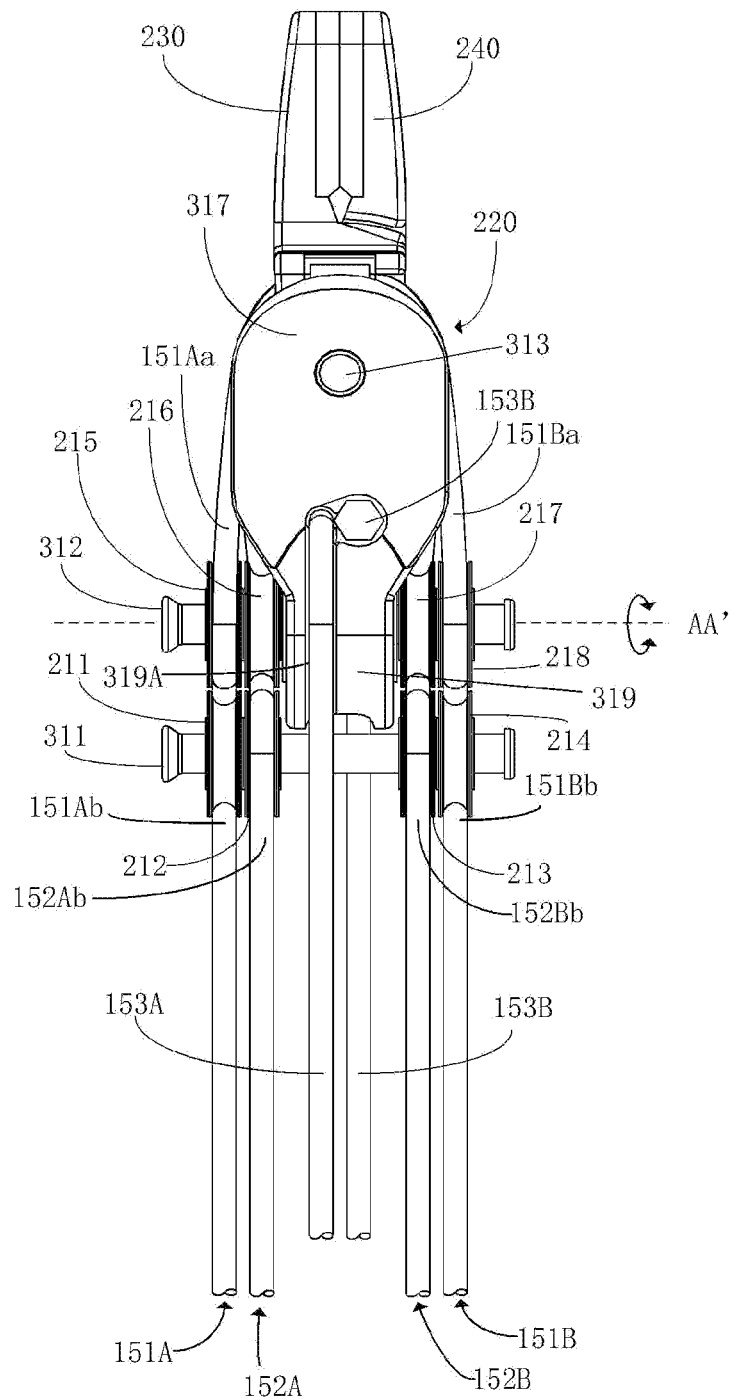

The first support member 210 is not shown in FIG. 5B and FIG. 5C for showing the proximal structure of the end effector 150 more clear. As shown in FIG. 5B and FIG. 5C, a first pair of pulleys is disposed on the first pin 311, the first pair of pulleys includes a first pulley 211, a second pulley 212, a third pulley 213 and a forth pulley 214 that are disposed on the first pin 311. A second pair of pulleys is disposed on the second pin 312, the second pair of pulleys includes a fifth pulley 215, a sixth pulley 216, a seventh pulley 217 and an eighth pulley 218, the first pulley 211, the second pulley 212, the third pulley 213, the forth pulley 214, the fifth pulley 215, the sixth pulley 216, the seventh pulley 217 and the eighth pulley 218 are all used for guiding of the driving cables. Because all the pulleys for guiding the driving cables are located on the first support member 210, there is no pulley on the second frame member 220, therefore, size of the second frame member 220 can be made smaller, such that size of the end effector 150 can be smaller, in addition, there is no risk of falling off of pulleys.

The second support member 220 includes a third pillar 317, a fourth pillar 318 and a pitch wheel 319, the third pillar 317 and the fourth pillar 318 are extending from the pitch wheel 319 toward the distal end of the end effector 150, the third pillar 317, the fourth pillar 318 and the pitch wheel form a clevis. The pitch wheel 319 of the second support member 220 is mounted on the second pin 312, the second support member 220 may rotate around an axis AA' of the second pin 312 so as to effect the pitch movement of the end effector.

A third pin 313 is disposed between the third pillar 317 and the forth pillar 318, an end of the third pin is fixed to the third pillar 317, the other end of the third pin 313 is fixed to the forth pillar 318, the third pin 313 is orthogonal to the first pin 311 and the second pin 312. The end effector 150 includes a first jaw 230 and the second jaw 240, the first jaw 230 and the second jaw 240 are pivotally mounted on the second frame member 220 through the third pin 313, the first jaw 230 and the second jaw 240 can rotate around an axis BB' of the third pin 313 so as to perform opening and closing movement, and/or yaw motion of the end effector 150, the first jaw 230 and the second jaw 240 can be a grasper for grasping tissue, stapler, or bipolar forceps.

As shown in FIG. 5A-5D, the direction identifier shown in FIGS. 5A and 5B are used for describing the winding manners of the driving cables on the end effector 150. The distal and proximal of the direction identifier respectively refer to the distal direction and proximal direction of the end effector 150, front, rear, left and right of the direction identifier respectively refer to front direction, rear direction, left direction and right direction of the end effector 150 in the view of FIG. 5A and FIG. 5B, although there is no direction identifier in other FIGS., but it is easy to derive the direction of the end effector 150 according to FIG. 5A and FIG. 5B, the driving cables disposed on the end effector 150 includes a first pair of cables, a second pair of cables and a third pair of cables, the first pair of cables and the second pair of cables are used for manipulating opening and closing movement, and/or yaw motion of the end effector 150, the third pair of cables are used for manipulating pitch movement of the end effector 150. The first pair of cables include a first driving cable 151A and a second driving cable 151B, the end of the first driving cable 151A and the end of the second driving cable 151B may be connected together or separated, so do the second pair of cables and the third pair of cables. The second pair of cables include a third driving cable 152A and a forth driving cable 152B, the third pair of cables include a fifth driving cables 153A and a sixth driving cable 153B. Referring to FIG. 5E, each of the driving cables include three segments, for example, the first driving cable 151A include a first segment 151A1, a second segment 151A2, and a third segment 151A3, the first segment 151A1 is extending into the driving apparatus, the second segment 151A2 is configured to the end effector 150, the third segment 151A3 is a rigid deformable 151A3 which is disposed between the first segment 151A1 and the second segment 151A2, such that the structure has higher transmission efficiency than using entire cable, and is hard to occur a situation of multiple driving cables intertwisted, in other embodiments, the driving cables may also be a complete and unsegmented cable.

On a side of end effector 150, the way of the first pair of cables wound around the first pair of pulleys and the second pair of pulleys is contrary to the way of the second pair of cables wound around the first pair of pulleys and the second pair of pulleys, the way of the first driving cable 151A wound around the first pair of pulleys and the second pair of pulleys is same with the second driving cable 151B wound around the first pair of pulleys and the second pair of pulleys, the third driving cable 152A wound around the first pair of pulleys and the second assembly is same with the way of fourth driving cable 152B wound around the first pair of pulleys and the second assembly. Specifically, the proximal end of the first driving cable 151A is connected to a driving unit inside of the driving apparatus 170, the distal end of the first driving cable 151A is extending to the distal end of the end effector 150 and fixed to the first jaw 230 via being guided by the front portion of the first pulley 211 and the rear portion of the fifth pulley 215. The distal end of second driving cable 151B is extending to the distal end of the end effector 150 and fixed to the first jaw 230 via being guided by the front portion of the fourth pulley 214 and the rear portion of the eighth pulley 218. The third driving cable 152A is extending to the distal end of the end effector 150 and fixed to the second jaw 240 via being guided by the rear portion of the second pulley 212 and the front portion of the sixth pulley 216. The distal end of the fourth driving cable 152B is extending to the distal end of the end effector 150 and fixed to the second jaw 240 via being guided by the rear portion of the third pulley 213 and the front portion of the seventh pulley 217.

The first driving cable 151A and the second driving cable 151B drive the first jaw 230 to rotate around the axis BB', the third driving cable 152A and the fourth driving cable 152B drive the second jaw 240 to rotate around the axis BB', wherein the first drives cable 151A, the second driving cable 151B, the third driving cable 152A and the fourth driving cable 152B drive the first jaw 230 and the second jaw 240 to perform the opening and closing movement and/or the jaw movement.

The proximal ends of the fifth driving cable 153A and the sixth driving cable 153B are connected to the driving apparatus 170, the distal end of the fifth driving cable 153A and the sixth driving cable 153B are received in a ring groove of the pitch wheel 319, the terminal ends of the fifth driving cable 153A and the sixth driving cable 153B are fixed in the second support member 220, the fifth driving cable 153A and the sixth driving cable 153B drive the second support 220 to rotate around axis AA', whereby rotational movement of the second support member 220 causes the jaw 230 and jaw 240 to perform pitch movement.

The structure and way of winding of driving cable of the end effector 150 are different from end effector of prior art, the first pair of pulleys of the end effector of the prior art is mounted on the first support member, the second pair of pulleys is mounted on the second support member, the second pair of pulleys performs pitch motion along with the second support member. In addition, the way of winding of the driving cable is different from the prior art, as shown in FIGS. 5A-5D, the first driving cable 151A has a first cable portion 151Aa which is between the fifth pulley 215 and the first jaw 230, the second driving cable 151B has a second portion cable 151Ba which is between the eighth pulley 218 and the first jaw 230, the third driving cable 152A has a third cable portion 152Aa which is between the sixth pulley 216 and the second jaw 240, the fourth driving cable 152B has a fourth portion cable 152Ba which is between the seventh pulley 217 and the first jaw 240. When the end effector 150 performs pitch motion, the first portion cable 151Aa and the second portion cable 151Ba are always on a side of a plane M, the third portion cable 152Aa and the fourth portion cable 152Ba are always on the other side of plane M, the plane M which is passing through the axis AA' of the second pin 312 and perpendicular to the axis BB' of the third pin 313, whereby winding of the first pair of cables and the second pair of cables on the end effector 150 is relatively simple, neat and easy to assemble.

Figure 5D:
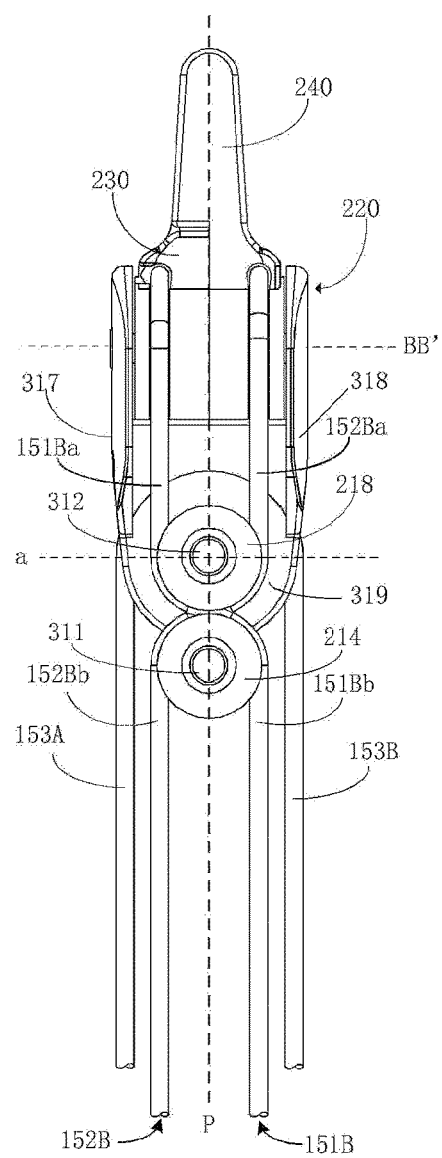
Figure 5E:
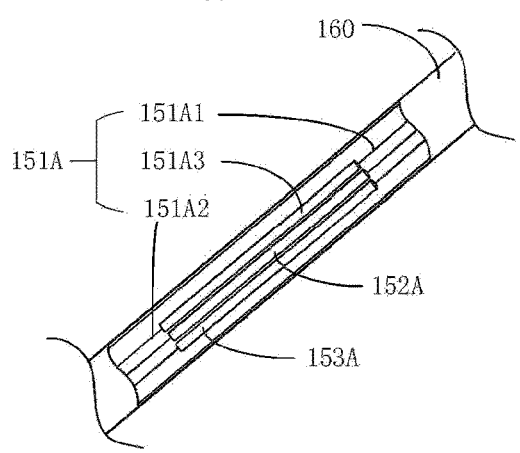
FIG. 5E is a schematic structural view of driving cables in an elongated shaft.

As shown in FIG. 5C and FIG. 5D, the first driving cable 151A has a fifth portion cable 151Ab which is between the first support member 210 and the first pulley 211 (the first support member 210 is not shown in FIG. 5C and FIG. 5D for showing driving cables), the second driving cable 151B has a sixth portion cable 151Bb which is between the first support member 210 and the fourth pulley 214, the third driving cable 152A has a seventh portion cable 152Ab which is between the first support member 210 and the second pulley 213, the fourth driving cable 152B has an eighth portion cable 152Bb which is between the first support member 210 and the third pulley 213, the fifth portion cable 151Ab and the sixth portion cable 151Bb are on a side of a plane P, the seventh driving cable 152Ab and the eighth portion cable 152Bb are on the other side of the plane P, the P is passing through the axis of the first pin 311 and the axis of the second pin 312.

Figure 6A:
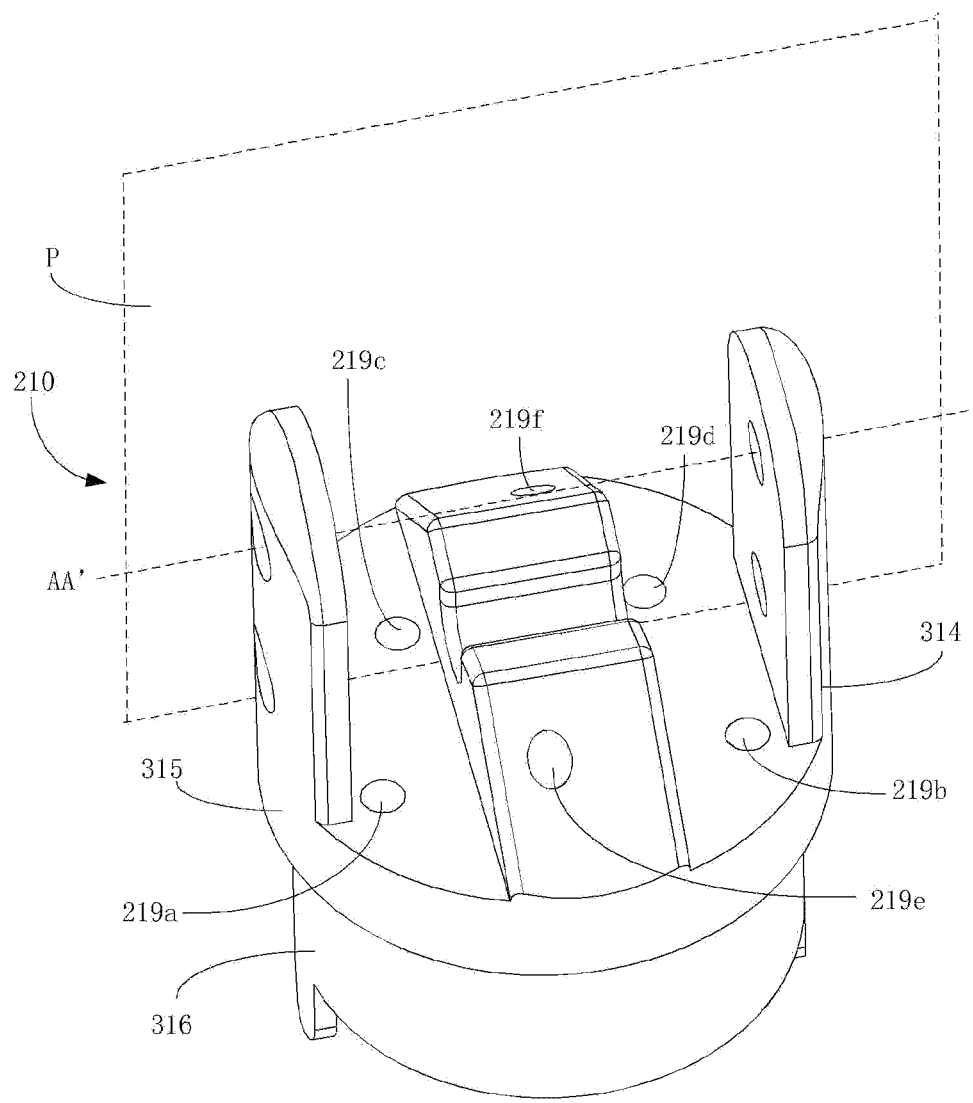
FIG. 6A is a perspective view of a first support member of an end effector according to an embodiment.
Figure 6B:
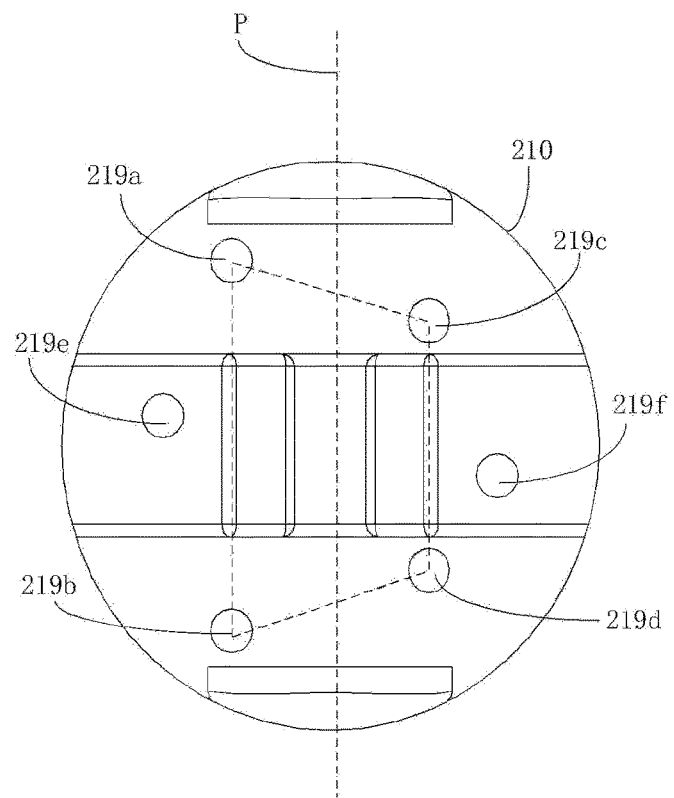
FIG. 6B is a top view of a first support member of an end effector according to an embodiment.

As shown in FIG. 6A and FIG. 6B, the chassis 316 of the first support member includes a plurality of holes configured for the driving cables to pass through, the plurality of holes include a first hole 219a used for the fifth portion cable 151Ab to pass through, a second hole 219b used for the sixth portion cable 151Bb to pass through, a third hole 219c used for the seventh portion cable 152Ab, a fourth hole 219d used for eighth portion cable 152Bb, a fifth hole 219e used for the fifth driving cable 153A to pass through, and a sixth hole 219f used for the sixth driving cable 153B to pass through. To cause the change of the first driving cable 152A, the second driving cable 152B, the third driving cable 152A and the fourth driving cable 152B is same when the end effector 150 performs pitch motion (such as length increasing or decreasing simultaneously), the first hole 219a and the second 219b are located on a side of the plane P, the third hole 219c and the fourth hole 219d are located on the other side of the plane P, a straight line which is passing through the center of the of the first hole 219a and the second hole 219b is parallel to a straight line which is passing through the center of the third hole 219c and the fourth hole 219d, the driving cables straightly extend to the first pair of pulleys via passing through holes of the chassis 316 because of the parallel relationship, such that the driving efficiency of the driving cables is efficient.

Referring to FIG. 6B, the first hole 219a, the second hole 219b, the third hole 219c, and the fourth hole 219d are respectively located on four vertices of a trapezoid, whereby the first driving cable 151A and the second driving cable 151B respectively pass through the first pulley 211 and the fourth pulley 214, the third driving cable 152A and the fourth driving cable 152B respectively pass through the second pulley 212 and the third pulley 213. To cause the loss of driving power of the fifth driving cable 153A and the sixth driving cable 153B is minimum when driving pitch motion of the end effector 150, the fifth hole 219e and the sixth hole 219f are located outside of the trapezoid formed by the first hole 219a, the second hole 219b, the third hole 219c, and the fourth hole 219d.

Figure 6C:
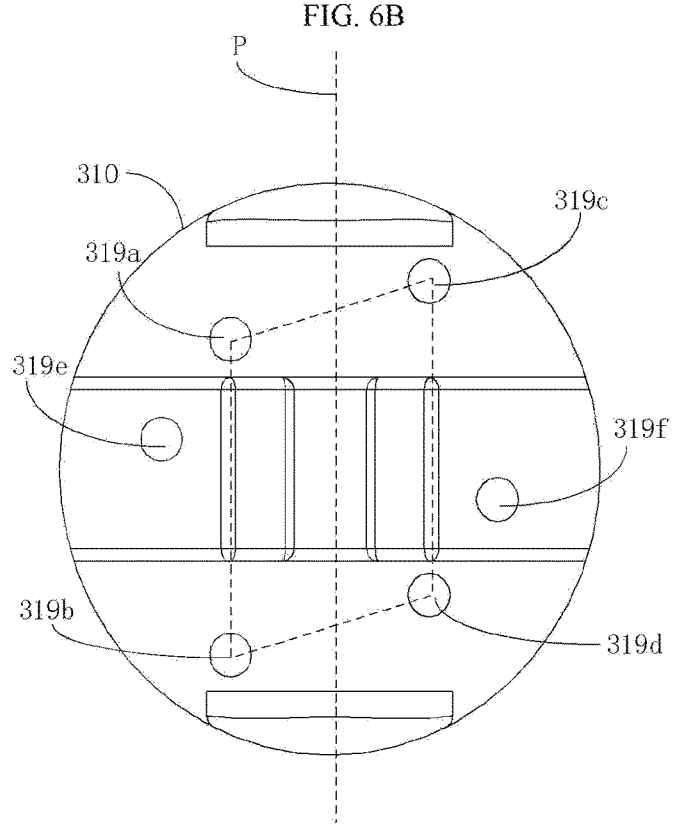
FIG. 6C is a top view of a first support member of an end effector according to another embodiment.

In an embodiment, referring to FIG. 6C, the first hole 219a, the second hole 219b, the third hole 219c, and the fourth hole 219d are respectively located on four vertices of a parallelogram, the fifth hole 219e and the sixth hole 219f are located outside of the parallelogram formed by the first hole 219a, the second hole 219b, the third hole 219c, and the fourth hole 219d.

In prior arts, the fifth portion cable of the first driving cable and the sixth portion cable of the second driving cable are located on different side of the plane P, the seventh portion cable of the third driving cable and the eighth portion cable of the fourth driving cable are located on the different side of the plane P, the hole used for the first driving cable to pass through and the hole used for the second driving cable to pass through located on different side of the plane P, the hole used for the third driving cable to pass through and the hole used for driving the fourth cable to pass through are located on the different side of the plane P. because the structure and way of winding of the end effector of present disclosure is different from the prior arts, the end effector of present disclosure is safer compared to the prior arts, the driving cables and the pulleys of present disclosure are not easy to fall off compared to the prior arts, assembly of the end effector of present disclosure is easy compared to the prior arts, the end effector of present disclosure is compact. Although the instrument of the present disclosure has the above advantages, but new challenges come with the instrument of present disclosure, that is the driving device of the prior art cannot drive the end effector of present disclosure, more specifically, the method of decoupling the coupling relationship between the third pair of cables with the first pair of cables and the second pair of cables of the prior arts is no longer suitable for end effector of present disclosure.

The coupling relationship between the third pair of cables with the first pair of cables and/or the second pair of cables of the end effector 150 is described as following. As showing in FIG. 5, a contact point where the first portion cable 151Aa is off the fifth pulley 215, a contact point where the second portion cable 151Ba is off the eighth pulley 218, a contact point where the third portion cable 152Aa is off the sixth pulley 216, a contact point where the fourth portion cable 152Ba is off the seventh pulley 217 are on a plane a, the plane a passes through the first axis AA' and perpendicular to the plane P.

Figure 7A:
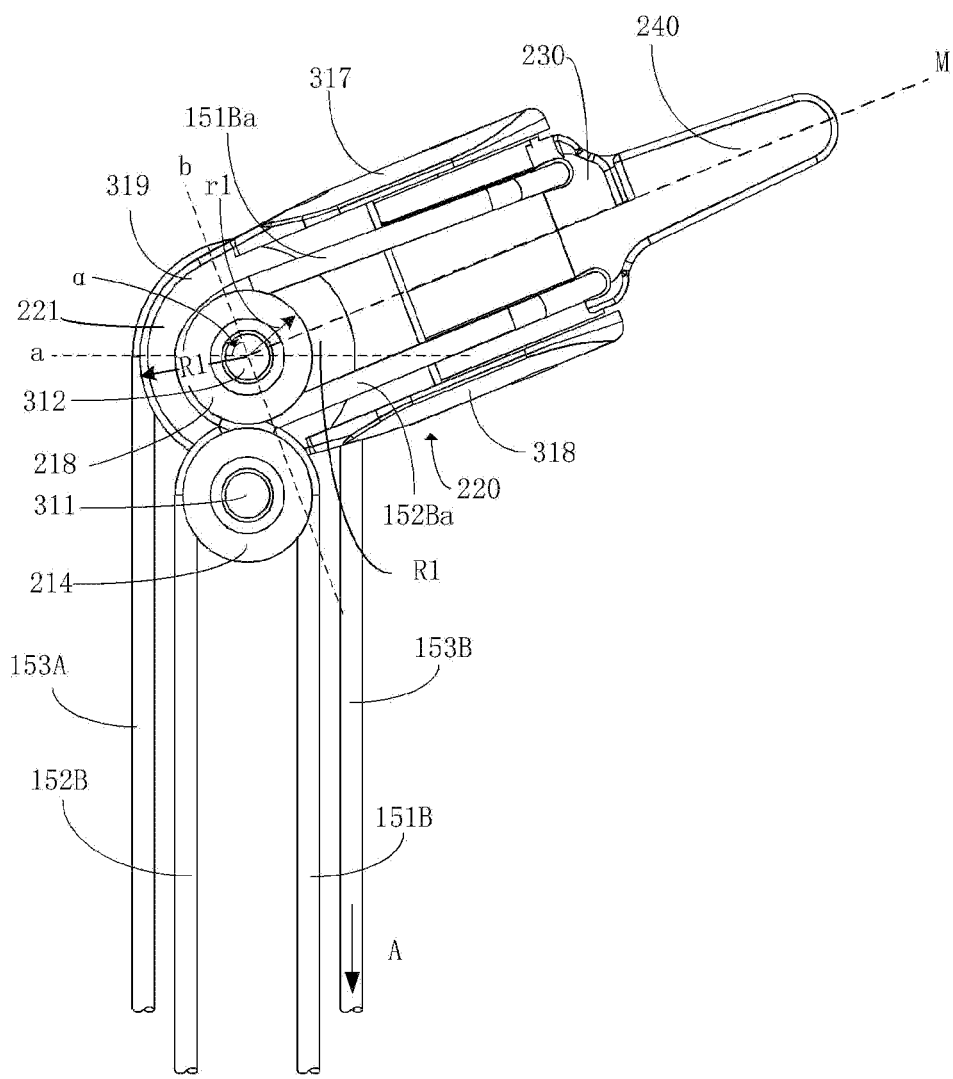
FIGS. 7A, 7B and 7C are schematic views of an end effector in a pitch state according to an embodiment.
Figure 7B:
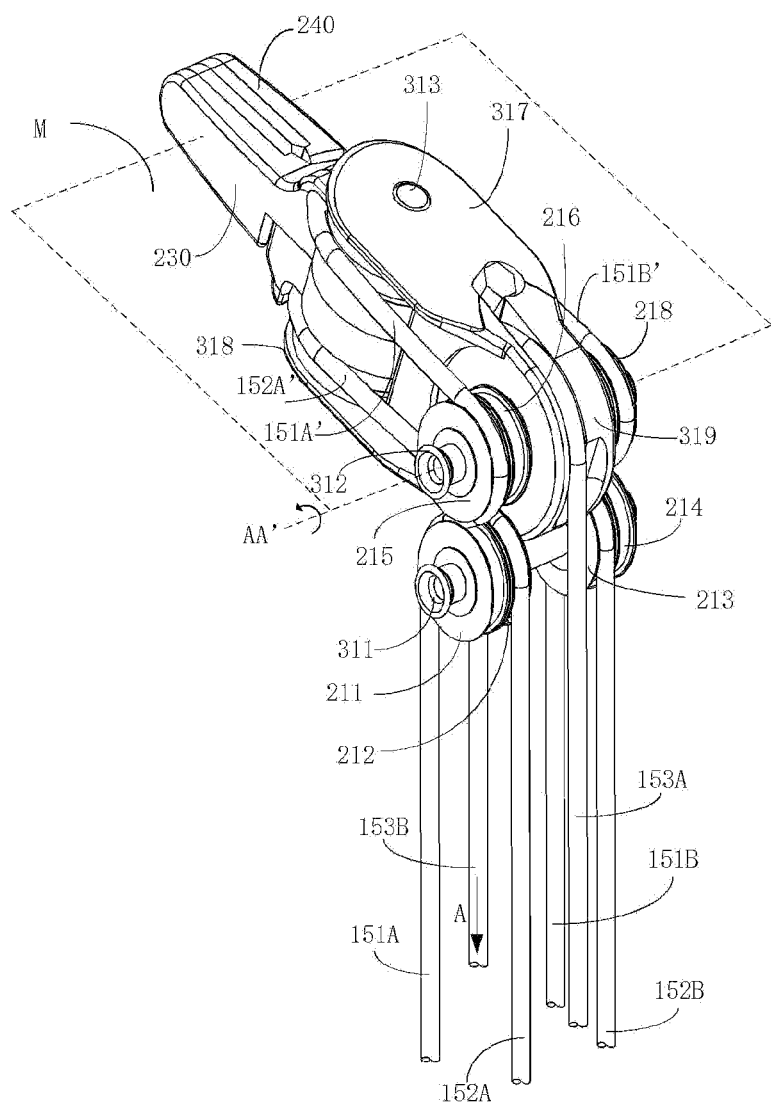
Figure 7C:
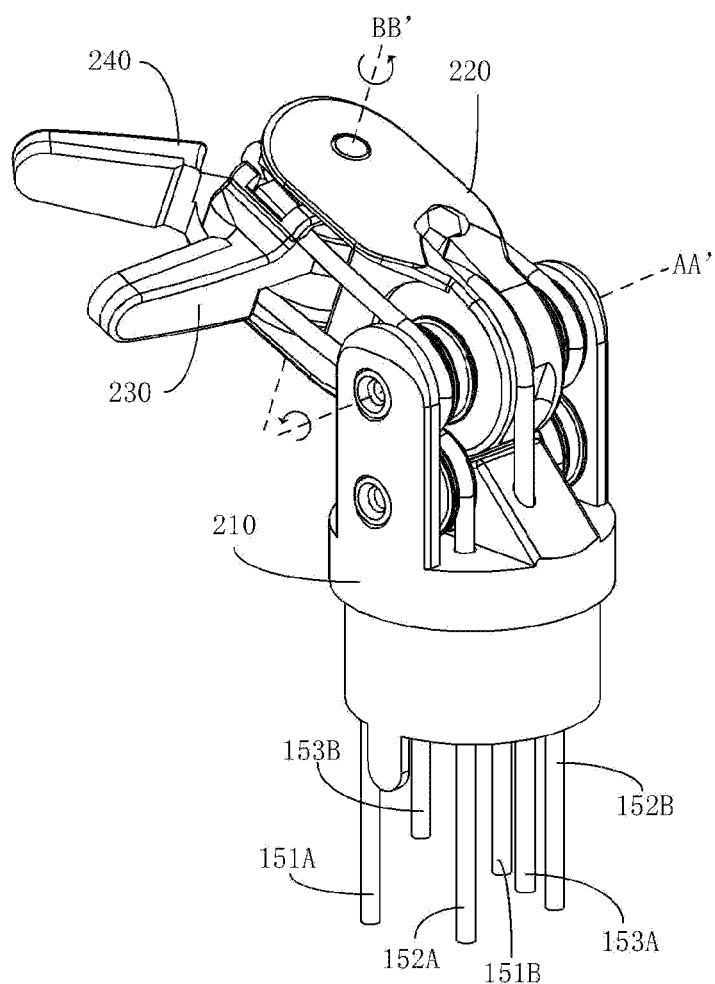

When the end effector 150 performs pitch motion, the driving apparatus 170 pulls the fifth driving cable 153A or the sixth driving cable 153B, so as to movement of the second support member 220 causes the first jaw 230 and the second jaw 240 rotate around the first axis AA' to perform pitch motion. As shown in FIG. 7A and FIG. 7B, the driving apparatus 170 pulls the sixth driving cable 153B, so as to the second support member 220, the first jaw 230 and the second jaw 240 performs pitch motion around the first axis AA' if the end effector 150 is only needed to perform pitch motion, it is necessary to keep length of the first portion cable 151Aa, the second portion cable 151Ba, the third portion cable 152Aa and the fourth portion 153Ba to be conserved, otherwise causing the yaw motion or the opening and closing movement of the end effector.

Figure 8A:
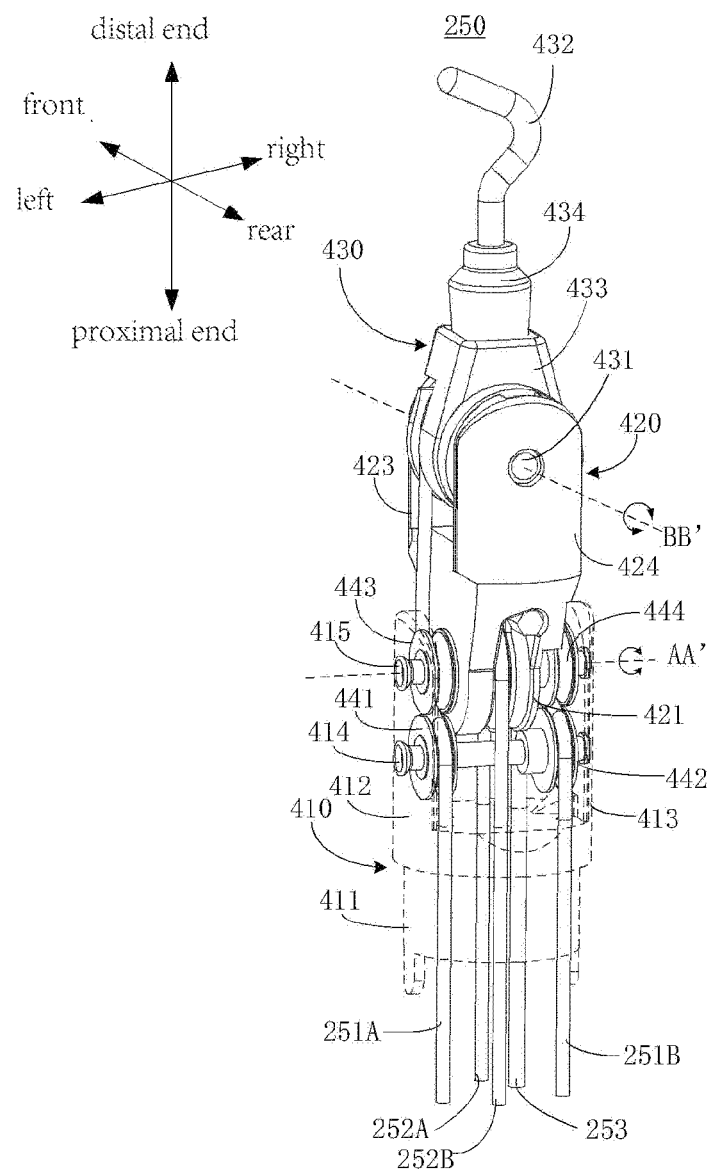
FIG. 8A is a perspective view of an end effector according to an embodiment.

In the process of the end effector 150 rotates from the straight state of shown in FIGS. 5A-5D to the pitch state shown in FIGS. 7A-7B, when the driving apparatus 170 pulls the sixth driving cable 153B, if a target pitch angle that the end effector 150 needs to be rotated is $\alpha$, the plane a shown in FIG. 5D needs to rotate a $\alpha$ angle so as to be the position of plane b shown in FIG. 7A, if radius of the first pair of pulleys and the second pair of pulleys are r1, to effect the target pitch angle of the effector 150 to be rotated is $\alpha$, the wrapping length of the first driving cable 151A wound around the fifth pulley 215 should be increased L, the wrapping length of the second driving cable 151B wound around the eighth pulley 218 should be increased L, the $L=\alpha*r_1$, the wrapping length of the third driving cable 152A and the fourth driving cable 152B respectively wound around the sixth pulley 216 and the seventh pulley 217 should be reduced L simultaneously. However, as shown in FIG. 8A, in the driving device, the first driving cable 151A and the second driving cable 151B are wound around a rotatable first driving unit 171 in a contrary way, the third driving cable 152A and the fourth driving cable 152B are wound around a rotatable second driving unit 172 in a contrary way, both of the first driving unit 171 and the second driving unit 172 are rotatably mounted the rotational axis, therefore the driving unit 171 and the second driving unit 172 cannot be translated, therefore the first driving cable 151A and the second driving cable 151B cannot be increased simultaneously or reduced simultaneously just only by rotation of the first driving unit 171, the third driving cable 152A and the fourth driving cable 152B cannot be increased simultaneously or reduced simultaneously just only by rotation of the second driving unit 172. As mentioned above, it is necessary that the length of the first driving cable 151A and the second driving cable 151B on the end effector 150 are increased simultaneously or reduced simultaneously, and the length of the third driving cable 152A and the fourth driving cable 152B on the end effector 150 are increased simultaneously or reduced simultaneously if the end effector 150 performs pitch motion, therefore movement of the third pair of cables is constrained to the first pair of cables and the second pair of cables.

The relationship of change of one element constrained to another element is referred to as a coupling relationship, that is, there is a coupling relationship between one element with another element. Regarding to the first pair of cables, the second pair of cables and the third pair of cables, a constrained relationship may be that the third pair of cables is constrained to the first pair of cables and/or the second pair of cables, therefore causing the third pair of cables cannot be moved, whereby the end effector cannot perform pitch motion, or movement of one of the first pair of cables, the second pair of cables or the third pair of cables may cause unexpected movement of another pair of cables, whereby the end effector cannot perform expected operation, for example, when the third pair of cables drive pitch motion of the end effector, because the coupling relationship between the third pair of cables with the first pair of cables and/or the second pair of cables, the movement of the third pair of cables causes the first pair of cables and/or the second pair of cables to be moved, whereby the pitch motion of the end effector causes the closing and opening movement and/or the yaw motion for the end effector, causing the pitch motion and the opening and closing movement and/or yaw motion effect to each other, the pitch motion and the opening and closing movement and/or yaw motion are not independent, so that the end effector cannot properly perform surgical operation. It is necessary that decouple the coupling relationship between the third pair of cables and the first pair of cables and/or the second pair of cables, so as to movement of the third pair of cables are no longer constrained to the first and/or the second pair of cables, the movements of the third pair of cables the first and/or the second pair of cables are independent to each other, without interference or impact on each other, decoupling the coupling relationship between the third pair of cables and the first and/or second pair of cables referred to as decoupling.

Figure 8B:
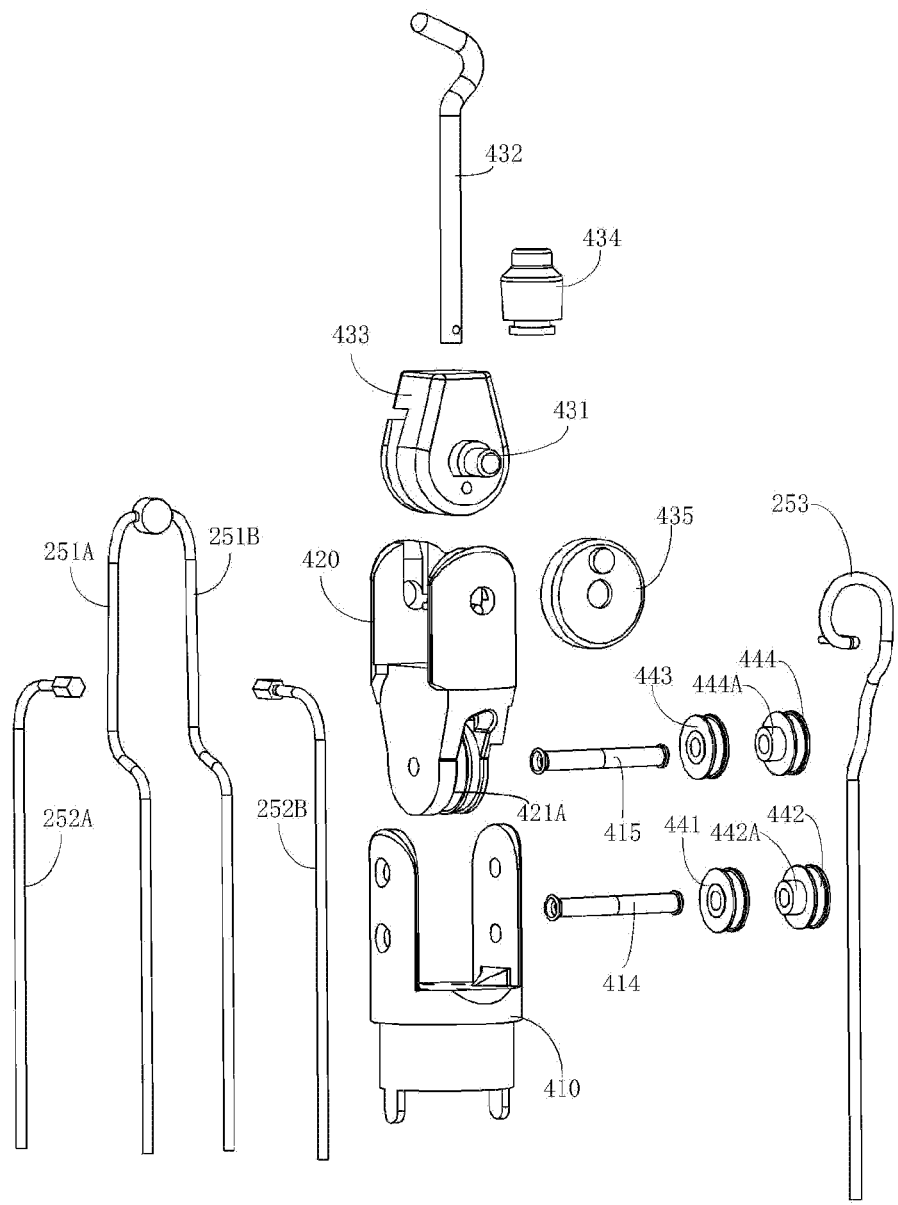
FIG. 8B is an exploded view of the end effector shown in the FIG. 8A.

As shown in FIGS. 8A and 8B, the end effector 250 in this embodiment is a single-pole cauterizing instrument, the end effector 250 includes a first frame 410, a second frame 420, and an executive component 430, and the first frame 410 and the second frame 420 are roughly U-shaped. The first frame 410 includes a chassis 411 and a first pillar 412 and a second pillar 413 extending from the chassis 411 along the distal end of the end effector 250, the proximal end of the chassis 410 is used for connecting the long shaft 160, and the second frame 420 is mounted between the first pillar 412 and the second pillar 413 of the first frame 410. The second frame 420 includes a pitch pulley 421 and a third pillar 423 and a fourth pillar 424 extending from the pitch pulley 421 along the distal end of the end effector 250, and the executive component 430 is mounted between the third pillar 423 and the fourth pillar 424. The executive component 430 in this embodiment is a single-pole cauterizing instrument, it will be appreciated that in other embodiments, the executive component 430 also be other execution tools, such as a cutter.

A first pin 414, a second pin 415, a first pair of pulleys, and second pair of pulleys of the first frame 410 are disposed between the first pillar 412 and the second pillar 413, the first pair of pulleys, and second pair of pulleys are used for guiding cables. The first pair of pulleys includes a first pulley 441 and a second pulley 442 sequentially disposed on the first pin 414, the second pair of pulleys includes a third pulley 443 and a fourth pulley 444 sequentially disposed on the second pin 415, the pitch pulley 421 of the second frame 420 is disposed on the second pin 414, and the pitch pulley 421 can rotate around the axis Aa' of the second pin 414 to perform the pitch movement of the end effector 250. A third pin 431 is disposed between the third pillar 423 and the fourth pillar 424 of the second frame 420, the executive component 430 is disposed on the third pin 431 and can rotate around the axis BB' of the third pin 431 to perform the yaw movement of the end effector 250, and the third pin 431 is perpendicular to the first pin 412 and the second pin 413.

The first pair of cables for manipulating the yaw movement of the end effector 250 includes a first driving cable 251A and a second driving cable 251B, the distal end of the first driving cable 251A is guided through the rear portion of the first pulley 441 and then continues to extend through the front portion of the third pulley 443 and then continues to extend to the distal end of the end effector 250 and is finally fixed to the executive component 430, and the distal end of the second driving cable 251B is guided through the rear portion of the second pulley 442 and then continues to extend through the front portion of the fourth pulley 444 and then continues to extend to the distal end of the end effector 250 and is finally fixed to the executive component 430. In other words, a part of the first driving cable 251A in contact with the third pulley 443 is between a part of the first driving cable 251A in contact with the first pulley 211 and with the executive component 430; a part of the second driving cable 151B in contact with the fourth pulley is between a part of the second driving cable 151B in contact with the second pulley 442 and with the executive component 430.

A second pair of cables for manipulating the pitch movement of the end effector 250 includes a third driving cable 252A and a fourth driving cable 252B, the pitch pulley has an annular groove to receive and guide the third driving cable 252A and the fourth driving cable 252B, the distal ends of the third driving cable 252A and the fourth driving cable 252B being received in the annular groove of the pitch pulley 421 and the ends being fixed in the second frame 420.

As shown in FIG. 8B, the end effector 250 further includes an electric cable 253 that provides power to the executive component 430, the second pulley 442 has a first guiding portion 442A that guides the electric cable 253, the fourth pulley 444 has a second guiding portion 443A that guides the electric cable 253, and the distal end of the electric cable 253 is connected to the executive component 430 after passing through the first guiding portion 442A of the second pulley 442 and the second guide 444A of the fourth pulley 444.

The executive component 430 includes an electric hook 432 and a first insulation member 433, a second insulation member 434, and a third insulation member 435 for preventing the electric hook 433 and the electric cable 253 from burning to an undesired portion, the proximal end of the electric hook 432 and the distal end of the electric cable 253 are connected in the first insulation member 433, the second insulation member 434 is connected to the distal end of the first insulation member 433, the end of the electric hook 432 is fixed in the second insulation member 434, and the distal end of the electric cable 253 is accommodated in the third insulation member 435 and extends into the first insulation member 433 to be connected to the proximal end of the electric hook 432.

Figure 8C:
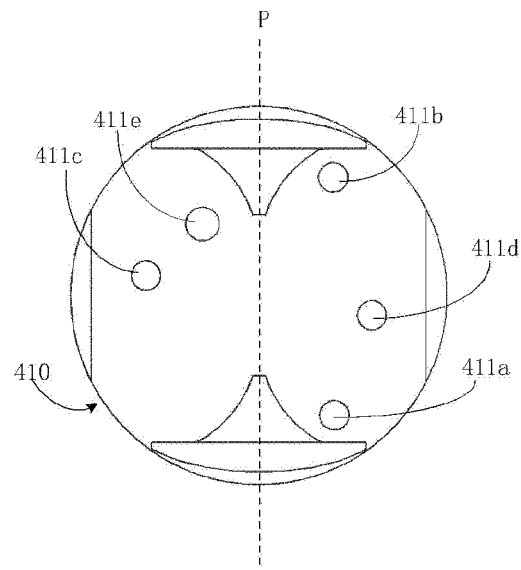
FIG. 8C is a top view of a second frame member shown in the FIG. 8A.

As shown in FIG. 8C, the chassis of the first frame 410 has a first through-hole 411a for passing through the first driving cable 251A, a second through-hole 411b for passing through the second driving cable 251B, a third through-hole 411c for passing through the third driving cable 252A, a fourth through-hole 411d for passing through the fourth driving cable 252b, and a fifth through-hole 411e for passing through the electric cable 253. Similar to the previous embodiment, the first through-hole 441a and the second through-hole 411b are located on the same side of the plane P through the axis of the first pin 414 and the second pin 415, and the third through-hole 411c and the fourth through-hole 411d are located on different sides of the plane P. The third through-hole 411c and the fourth through-hole 411d are located on the same side of the plane P, so that the winding manner of the first pair of cables on the end effector 250 is simple, and the assembly is easy.

Figure 8D:
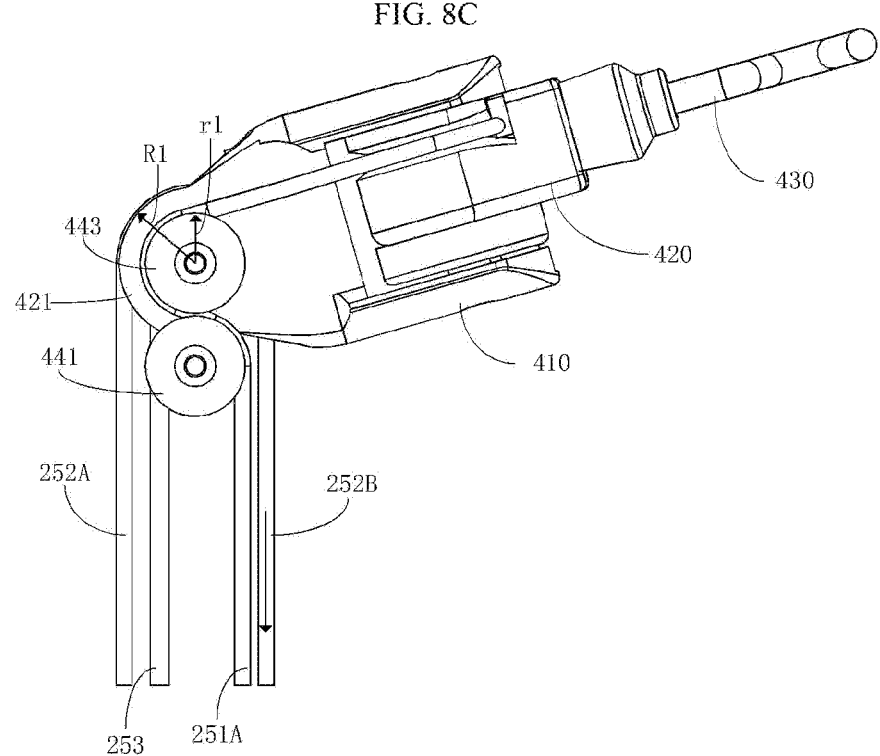
FIG. 8D is a schematic view of a pitch state of the end effector shown in FIG. 8A.
Figure 8E:
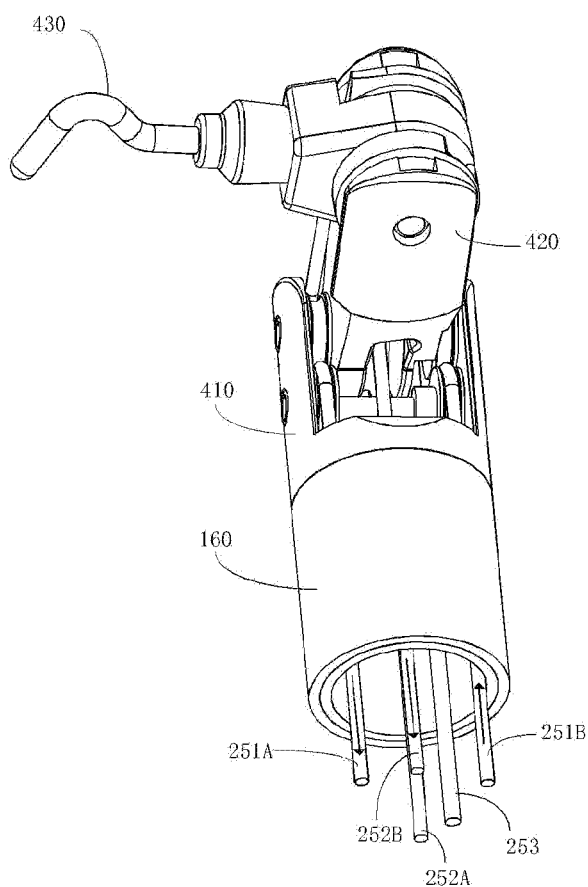
FIG. 8E is a schematic view of a pitch and yaw state of the end effector shown in FIG. 8A.

As shown in FIG. 8D, when the driving apparatus of the end effector 250 pulls the fourth driving cable 252B and releases the third driving cable 252A, the end effector 250 performs the pitch movement as shown in FIG. 8D, when the driving apparatus of the end effector 250 pulls the fourth driving cable 252B and releases the first driving cable 251A and second driving cable 251B, the end effector 250 performs the pitch movement and yaw movement as shown in FIG. 8E. Same as the previous embodiment, the second pair of cables for manipulating the pitch movement of the end effector 250, and the first pair of cables for manipulating the yaw movement of the end effector 250 also have a coupling relationship, i.e., the movement of the third driving cable 252A and the fourth driving cable 252B is limited by the first driving cable 251A and the third driving cable 251B.

For how to release the coupling relationship between the driving cables in the two embodiments, taking the end effector in the embodiment shown in FIG. 5A as an example, the existing decoupling method is decoupled by using a software algorithm, and the main operation console 200 controls the third driving unit to drive the third pair of cables to move, and also controls the first driving unit and the second driving unit to drive the first pair of cables and the second pair of cables to move, so as to increase or decrease the wrapping length of the first pair of cables and the second pair of cables on the pulleys with the movement of the third pair of cables. But the decoupling method needs the first portion 151Aa and the second portion 151Ba of the first pair of cables each disposed on the opposite side of the plane M, the third portion 152Aa and the fourth portion 152Ba of the second pair of cables also each disposed on the opposite side of the plane M, such that the first driving cable 151A and the second driving cable 151B of the first pair of cables form a loop spanning the plane M, and the third driving cable 152A and the fourth driving cable 152B of the second pair of cables also form a loop spanning the plane M to achieve decoupling by controlling the movement of the driving unit by software. However, the first portion 151Aa and the second portion 151Ba of the first pair of cables on the end effector of the embodiment shown in FIG. 5A of the present disclosure are located on the same side of the plane M, and the third portion 153Aa and the fourth portion 153Ba of the second pair of cables are also located on the same side of the plane M, so that the existing software decoupling method cannot decouple the end effector of this type. In Addition, the method for decoupling by using a software algorithm can lead to complex and error-prone control procedures for surgical robots, and each driving unit of the driving mechanism of the surgical instrument to lose independence, specifically, the driving apparatus is internally provided with three driving units which respectively drive three pairs of cables, and the control of each driving unit in an ideal condition is independent of each other; however, when a software algorithm is used for decoupling, the three driving units need to be controlled to move together at the same time, so that the three driving units lose independence, and control errors are easy to occur.

The present disclosure proposes a mechanical decoupling solution, and a mechanical decoupling member is provided in the driving apparatus 170 of the surgical instrument 120, thereby avoiding the disadvantage of decoupling the software algorithm as described above.

As shown in FIG. 9A, which is a schematic view of a driving apparatus 170 according to an embodiment of the present disclosure, the driving apparatus 170 is suitable for driving the end effector shown in FIG. 5A. The driving apparatus 170 includes a first driving unit 171 and a second driving unit 172 for driving the end effector 150 to perform opening and closing and/or yawing movement, a third driving unit 173 for driving the end effector 150 to pitch, and a fourth driving unit 174 for driving the long shaft 160 to rotate. The first driving cable 151A and the second driving cable 151B of the first pair of cables are wound on the first driving unit 171 in an opposite winding manner, the third driving cable 152A and the fourth driving cable 152B of the second pair of cables are wound on the second driving unit 172 in an opposite winding manner, the fifth driving cable 153A and the sixth driving cable 153B of the third pair of cables are wound on the third driving unit 173 in an opposite winding manner, and the seventh driving cable 154A and the eighth driving cable 154B are wound on the fourth driving unit 174 in an opposite winding manner.

When the actuator driving shaft 171A in the instrument mounting frame 132 rotates to drive the first driving unit 171 to rotate along with its axis, the first driving unit 171 pulls or releases the first driving cable 151A or the second driving cable 151B to rotate the first clamping portion 230 around the third pin 313, and when the actuator in the instrument mounting frame 132 drives the second driving unit 172 to rotate along with its axis 172A, the second driving unit 172 pulls or releases the second driving cable 152A or the third driving cable 152B to rotate the second clamping portion 240 around the third pin 313, the first clamping portion 230 and the second clamping portion 240 rotate around the third pin 313, such that the end effector perform the opening and closing and/or yawing movement. When the actuator drive shaft 173A in the instrument mounting frame 132 rotates to drive the third driving unit 173 to rotate, the third driving unit 173 pulls or releases the fifth driving cable 153A or the sixth driving cable 153B to rotate the second frame 220 around the axis AA' of the second pin 312 to perform the pitch movement of the end effector 150. When the actuator in the instrument mounting frame 132 drives the fourth driving unit 174 to rotate along with its axis 174A, the fourth driving unit 174 pulls or releases the seventh driving cable 154A or the eighth driving cable 154B to drive the rotation of the long shaft 160.

The driving apparatus 170 further comprises a decoupling member for releasing the coupling relationship between the third pair of cables and each of the first pair of cables and the second pair of cables on one side of the end effector 150, the decoupling member comprises a main decoupling element 1761 and a slave decoupling element 176, the slave decoupling element 176 comprises a carriage 1762 and a first guiding portion 1763 and a second guiding portion 1764 connected to both ends of the carriage 1762, the main decoupling element 1761 is connected to the carriage 1762 through the first decoupling cable 1767 and the second decoupling cable 1768, and the main decoupling element 1761 further manipulates the movement of the slave decoupling member by driving the first decoupling cable 1767 and the second decoupling cable 1768. The first decoupling cable 1767 and the second decoupling cable 1768 are wound on the main decoupling element 1761 in an opposite manner, the main decoupling element 1761 and the third driving unit 173 move at the same angular velocity, and the main decoupling element 1761 and the third driving unit 173 may be disposed on the same shaft 173A, so that the main decoupling element 1761 and the third driving unit 173 rotate coaxially with the shaft 173A. In other embodiments, the main decoupling element 1761 and the third driving unit 173 also can be disposed on different rotating shafts. The main decoupling element 1761 and the third driving unit 173 have different radii, the radius of the main decoupling element 1761 is r2, the radius of the third driving unit 173 is R2, wherein, r2<R2, the main decoupling element 176 drives the slave decoupling element to move through polling or releasing the first decoupling cable 1767 or second decoupling cable 1768. The main decoupling element 1761 and the third driving unit 173 can receive drives from the same power source, i.e., the actuator of the slave operation device. In other embodiments, the main decoupling element and the third driving unit are disposed on different rotating shafts, however, the main decoupling element still receive drives from the same power source as the third driving unit, for example, the same actuator, is connected to and drives the main decoupling element and the third driving unit respectively in different manners, and the same power source is used to simultaneously drive the third driving unit and the main decoupling element, so that the decoupling control is simpler, the decoupling member does not need to separately re-detect the coupling state, and the main decoupling element and the coupling source (i.e., the third driving unit) receive the same control information, and the structures on the transmission side are different.

As shown in FIG. 9A, the first driving cable 151A and the second driving cable 151B sequentially extend into the long shaft after being guided by the third guiding pulley 177A, the first guiding portion 1763, and the third guiding pulley 177C, and then extend all the way to the end effector 150. The driving cable 152A and the fourth driving cable 152B sequentially extend into the long shaft after being guided by the second guiding pulley 177B, the second guiding portion 1764, and the fourth guiding pulley 177D, and then extend all the way to the end effector 150. The fifth driving cable 153A and the sixth driving cable 153B respectively extend into the long shaft after being guided by the fifth guiding pulley 177E and the sixth guiding pulley 177F and then extend to the end effector 150, and how the first driving cable 151A to the sixth driving cable 153B are connected to the end effector 150 has been described in detail, and details are not described herein again.

Figures 9D, 9E:
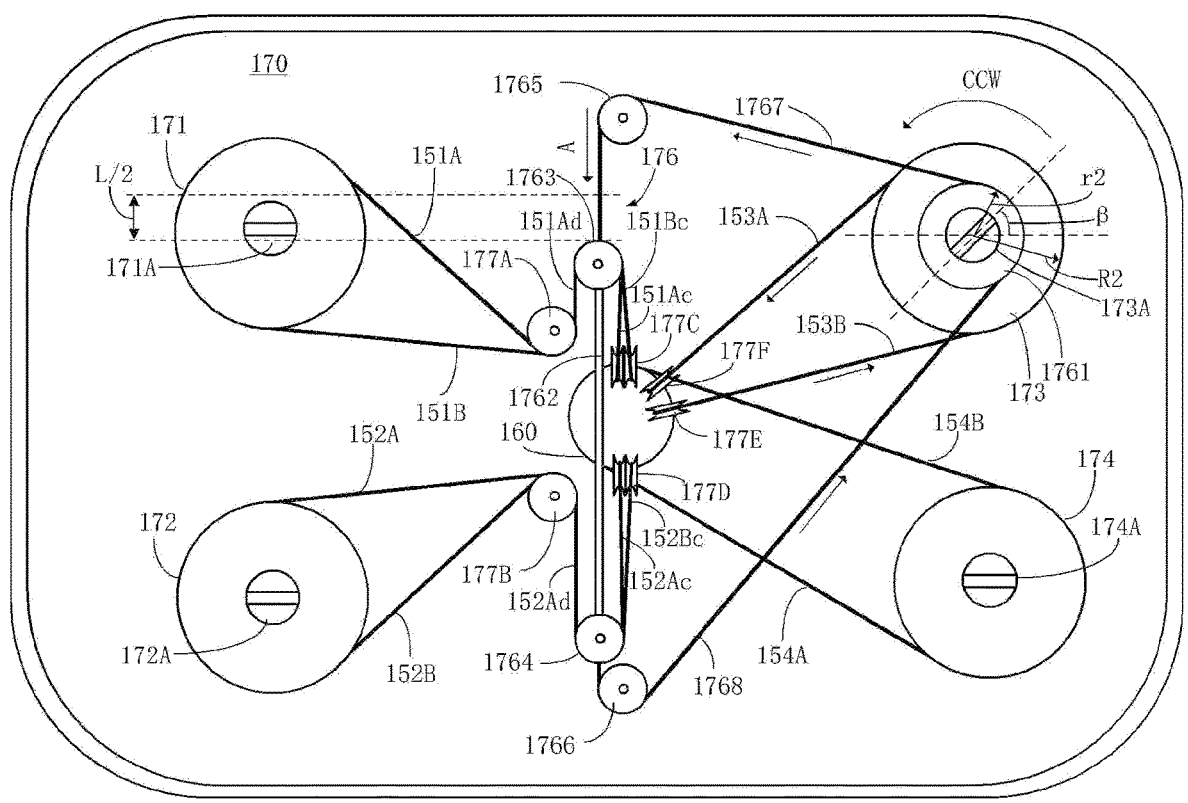
FIGS. 9D-9E are schematic views of a decoupling process of the driving apparatus shown in FIG. 9A.

As shown in FIG. 9D, when the third driving unit 173 rotates in a counter-clockwise (first direction) with its axis 173A, the third driving unit 173 pulls the sixth driving cable 153B and simultaneously releases the fifth driving cable 153A, such that the second frame 220 of the end effector 150 performs a pitch movement by rotating about the axis AA' of the second pin 312 as FIGS. 7A and 7B. As described above, at this time, the wrap angle lengths of the first driving cable 151A and the second driving cable 151B respectively on the fifth pulley 215 and the eighth pulley 218 need to be increased by L, and at the same time, the wrapping lengths of the third driving cable 152A and the fourth driving cable 152B on the sixth pulley 216 and the seventh pulley 217 need to be reduced L simultaneously, so that the end effector 150 can perform the pitch movement. Since the main decoupling element 1761 and the third driving unit 173 of the decoupling member both rotate about the shaft 173A, the main decoupling element 1761 also rotates counter-clockwise along the shaft 173A while the third driving unit 173 rotates counter-clockwise with the shaft 173A, at this time, the main decoupling element 1761 pulls the first decoupling cable 1767 and simultaneously releases the second decoupling cable 1768. When the main decoupling element 1761 turns through an arc of length L/2, the slave decoupling element is pulled by the first decoupling cable 1767 by a distance L/2 in the direction A. At this point, due to the movement of the slave decoupling element, the length of the first driving cable 151A and second driving cable 151B within the driving apparatus 170 will simultaneously decrease by L, that is, the length of the first pair of cables within the driving apparatus 170 is reduced by 2L. Accordingly, the length of the third driving cable 152A and the fourth driving cable 152B within the driving apparatus 170 will increase L simultaneously, that is, the length of the second pair of cables within the driving apparatus 170 is increased by 2L.

Thus, the length reduction amount of the first driving cable 151A and the second driving cable 151B in the driving apparatus 170 is equal to the required increase in wrapping length of the first driving cable 151A and the second driving cable 151B on the fifth pulley 215 and the eighth pulley 218 respectively, and the increase in length of the third driving cable 152A and the fourth driving cable 152B in the driving apparatus 170 is equal to the required reduction in wrapping length of the third driving cable 152A and the fourth driving cable 152B on the sixth pulley 216 and the seventh pulley 217. Conversely, as shown in FIG. 9E, when the third driving unit 173 and the main decoupling element 1761 rotate clockwise (the second direction), the length increase amount of the first driving cable 151A and the second driving cable 151B in the driving apparatus 170 is equal to the required reduction in wrapping length of the first driving cable 151A and the second driving cable 151B on the fifth pulley 215 and the eighth pulley 218 respectively, and the length reduction amount of the third driving cable 152A and the fourth driving cable 152B in the driving apparatus 170 is equal to the required increase in wrapping length of the third driving cable 152A and the fourth driving cable 152B on the sixth pulley 216 and the seventh pulley 217. Therefore, the length variation of the first pair of cables and the second cable on one side of the end effector caused by the pitch movement of the end effector is completely provided by the length change of the first pair of cables and the second cable in the driving apparatus, so that the movement of the third pair of cables is no longer limited by the first pair of cables and the second pair of cables, and the decoupling member realizes the release of the coupling relationship between the third pair of cables and the first pair of cables and the second pair of cables.

In order to release the coupling relationship between the first pair of cables and the second pair of cables and the third pair of cables accurately and controllably, the main decoupling element 1761 of the decoupling member drives the slave decoupling element 176 to move along a straight line all the time, and the length change of the first driving cable 151A, the second driving cable 151B, the third driving cable 152A, and the fourth cable 152B caused by the movement of the decoupling element 176 is always linear. As shown in 9A-9C, the first decoupling cable 1767 is redirected by the seventh guiding pulley 1765 and then fixed to one end of the slave decoupling element 176 in the direction of motion from the slave decoupling piece 176, similarly, the second decoupling cable 1768 is redirected by the eighth guiding pulley 1766 and then fixed to the other end of the slave decoupling element 176 in the direction of motion from the slave decoupling piece 176, so that the movement of the main decoupling element 1761 will cause the decoupling piece 176 to move linearly. The portion of the first decoupling cable 1767 between the seventh guiding pulley 1765 and the slave decoupling element 176 and the portion of the second decoupling cable 1768 between the eighth guiding pulley 1766 and the slave decoupling element 176 are parallel to the motion direction of the slave decoupling element 176, and in the decoupling process, the length change speed of the first decoupling cable 1767 and the second decoupling cable 1768 is proportional to the rotational linear speed of the main decoupling element 1761, so that the decoupling process can be precisely controlled.

As shown in FIGS. 9B-9C, the first guiding pulley 177A, the first guiding portion 1763, and the third guiding pulley 177C are all have two pulleys set side-by-side, the two pulleys are respectively configured to guide the first driving cable 151A and the second driving cable 151B. A first decoupling portion cable 151Ac is formed from the part between the third guiding pulley 177C and the first guiding portion 1763 of the first driving cable 151A, a third decoupling portion cable 151Ad is formed between the first guiding portion 1763 and the first guiding pulley 177A of the first driving cable 151A, a second decoupling portion cable 151Bc is formed from the part between the third guiding pulley 177C and the first guiding portion 1763 of the second driving cable 151B, a fourth decoupling portion cable 151Bd is formed from the part between the first guiding portion 1763 and the first guiding pulley 177A of the second driving cable 151B. Likewise, the second guiding portion 1764, the second guiding pulley 177 B and the fourth guiding pulley 177D are all also have two pulleys set side-by-side. The third driving cable 152A has a fifth decoupling portion cable 152Ac between the fourth guiding pulley 177D and the second guiding portion 1764, the fourth driving cable 152B has a sixth decoupling portion cable 152Bc between the fourth guiding pulley 177D and the second guiding portion 1764, a seventh decoupling portion cable 152Ad between the second guiding portion 1764 and the third guiding pulley 177B, and an eighth decoupling portion cable (in FIGS. 9A, the seventh decoupling portion cable 152Ad shield is obscured and invisible) between the second guiding portion 1764 and the third guiding pulley 177B. To enable more accurate decoupling, the length variation of the first decoupling part cable 151Ac and the length variation of the second decoupling part cable 151Bc need to be equal in the decoupling process, so that the first decoupling part cable 151Ac and the second decoupling part cable 151Bc each form the same angle θ with a plane, which passes through the centre of the third guiding pulley 177C and is perpendicular to the axis c1 of the third guiding pulley 177C, and the fifth decoupling part cable 152Ac, the seventh decoupling part cable 152Bc and the seventh guiding pulley 177D also have the same arrangement, so that the length variation of the first decoupling part cable 151Ac and the second decoupling part cable 151Bc in the decoupling process can be the same, and the length variation of the fifth decoupling portion cable 152Ac and the seventh decoupling portion cable 152Bc in the decoupling process can be the same. In Addition, since the θ is small, the first decoupling part cable 151Ac and the second decoupling part cable 151Bc are approximately equal to the shaft spacing H1 of the first guiding pulley 1764 and the fourth guiding pulley 177B, and in the decoupling process, the first decoupling part cable 151Ac and the second decoupling part cable 151Bc are approximately parallel to the movement direction of the slave decoupling element, so that the nonlinear change of the first decoupling part cable 151Ac and the second decoupling part cable 151Bc in the decoupling process caused by the first decoupling part cable 151Ac and the second decoupling part cable 151Bc is relatively small, so as to achieve more accurate decoupling process.

As shown in FIG. 9C, the third decoupling portion cable 151Ad, the fourth decoupling portion cable 151Bd, the seventh decoupling portion cable 152Ad, and the eighth decoupling portion cable are parallel to the movement direction of the slave decoupling element 176, such that the length change speed of the third decoupling portion cable 151Ad, the fourth decoupling portion cable 151Bd, the seventh decoupling portion cable 152Ad, and the eighth decoupling portion cable caused by the movement of the decoupling member during the decoupling process is proportional to the speed of movement from the decoupling element 176, so that in the decoupling process, the length change speed of any one of the first driving cables 151A to the fourth driving cable 152B in the driving apparatus 170 is proportional to the movement speed of the slave decoupling element 176, and from the above, the movement speed of the slave decoupling element 176 is proportional to the rotational linear speed of the main decoupling element 1761 and the third driving unit 173. Therefore, in the decoupling process, the length change speed of any one of the first driving cables 151A to the fourth driving cable 152B in the driving apparatus 170 is also proportional to the rotational linear speeds of the main decoupling element 1761 and the third driving unit 173, so that the length variation of the first pair of cables and the second pair of cables on the end effector 150 is precisely controlled by the main decoupling element 173 and the third driving unit 173, enabling the decoupling process controlled accurately.

As shown in FIG. 9D, with respect to the state shown in 9A, When the main decoupling element 1761 rotates counterclockwise by L/2 arc length, the slave decoupling element 176 moves accordingly by L/2 distance in the A-direction, the lengths of the first decoupling part cable 151Ac, third decoupling portion cable 151Ad, and second decoupling portion cable 151Bc, and the fourth decoupling portion cable 151Bd are simultaneously reduced by L/2, so that the first driving cable 151A and the second driving cable 151B simultaneously decrease in length L within the driving apparatus 170, that is, the length of the first pair of cables in the driving apparatus is reduced by 2L. Similarly, the fifth decoupling portion cable 152Ac, the sixth decoupling portion cable 152Ad, the seventh decoupling portion cable 152Bc, and the eighth decoupling portion cable are simultaneously increased 112, so that the third driving cable 152A and the fourth driving cable 152B simultaneously increase the length L within the driving apparatus 170, i.e., the length of the second pair of cables within the drive device increases by 2L.

Returning again to FIG. 7A, when the radius of the second pair of pulleys is r1 in this embodiment, the annular groove 319A in the pitch pulley 319 of the second frame 220 for accommodating and guiding the fifth driving cable 153A and the sixth driving cable 153B has a groove bottom radius of R1, and when the end effector 150 is pitching, the fifth driving cable 153A or the sixth driving cable 153B can form a wrap angle in the annular groove. During the rotation of the end effector 150 from the zero state shown in FIG. 5D to the state shown in FIG. 7A, when the pitch angle of the end effector 150 is α, the wrapping length of the fifth driving cable 153A in the annular groove 319A on the pitch pulley 319 is increased by L1, and the wrapping length of the sixth driving cable 153B in the annular groove 319A on the pitch pulley 319 is decreased by L1, where L1=α*R1, since the pitching movement of the end effector 150 is driven by the third driving unit 173 within the driving apparatus 170. As shown in FIG. 9D, at this point, when the angle turned by the third driving unit 173 to cause the end effector 150 to perform the pitch movement at an angle α along the counterclockwise (first direction) is β. The third driving unit 173 releases the fifth driving cable 153A and pulls the sixth driving cable 153B at the same time, so that the length of the fifth driving cable 153A around the third driving unit 173 is reduced by L1, and the length of the sixth driving cable 153B around the third driving unit 173 is increased by L1, where L1=β*R2. Since the main decoupling element 1761 and the third driving unit 173 rotate coaxially, the main decoupling element 1761 releases the first decoupling cable 1767 and pulls the second decoupling cable 1768, so that the length of the first decoupling cable 1767 wound around the main decoupling element 1761 is reduced by L/2, that is, the first decoupling cable 1767 is released by L/2 and the length of the second decoupling cable 1768 wound around the main decoupling element 1761 is increased by L/2, where L/2=β*R2, so that the carriage 1762 is moved by a distance L/2 in the A-direction, so that the lengths of the first driving cable 151A and the second driving cable 151B in the driving apparatus 170 are respectively reduced by L, and the length of the third driving cable 152A and the length of the fourth driving cable 152B in the driving apparatus 170 are respectively increased by L, it can be shown that, L=α*r1. In summary, by means of the four equation above: L1=α*R1, L1=β*R2, L/2=β*r2, L=α*r1, may obtain the following relationship:

$$\frac{R2}{r2} = 2\frac{R1}{r1}$$

The above relationship shows that the ratio of the radius of the third driving unit 173 to the radius of the main decoupling element 1761 is twice as the ratio of the groove bottom radius of the annular groove 319A of the pitch pulley 319 to the radius of the second pair of pulleys. The 2-fold relationship is caused by the fact that the slave decoupling element has two guiding portions, that is, a first guiding portion 1763 and a second guiding portion 1764. In other embodiments, the number of the guiding portions of the slave decoupling element 176 can be other, so that the ratio of the radius of the third driving unit to the radius of the main decoupling element and the ratio of the radius of the pitch pulley to the radius of the second pair of pulleys is thus varied, for example, the slave decoupling element may have N guiding portions, the ratio of the radius of the third driving unit to the radius of the main decoupling element is N times the ratio of the groove bottom radius of the annular groove of the pitch pulley to the radius of the second pair of pulleys, that is:

$$\frac{R2}{r2} = N\frac{R1}{r1},$$

However, the increase in the number of guiding portions of the slave decoupling element results in the size of the slave decoupling element, the above mentioned embodiment uses 2 guiding portions from the slave decoupling element. It will be understood that both the radius of the driving unit and the radius of the main decoupling element described above refer to the radius of the part of the driving cable or uncoupling cable wrapped around it, e.g. the radius of the winch, the radius of the pulley refers to the groove bottom radius of the pulley, by this can calculate the wrapping length of the driving cable wound around the pulley, although the radius of the pulley is interpreted differently in different literature (e.g. radius of the bottom groove, radius of the bottom of the groove), the radius of the pulley in the disclosure is the parameter used to measure the length of the wrap angle of the driving cable around the pulley.

Therefore, the length variation of the first pair of cables and the second pair of cables on one side of the end effector 150 required for the pitch movement of the end effector 150 is completely provided by the decoupling element 176 causing the length variation of the first pair of cables and the second pair of cables in the driving apparatus 170, so that the movement of the third pair of cables is no longer limited by the first pair of cables and the second pair of cables, enabling a precise decoupling between the third pair of cables and the first pair of cables and the second pair of cables. In the whole decoupling process, the length of the first portion 151Aa, the second portion 151Ba, the third portion 152Aa, and the fourth portion 153Ba can be kept constant all the time, the tensioning degree of the first pair of cables and the second pair of cables is always kept unchanged, and in the whole decoupling process, only the shaft 173A of the third driving unit 173 moves, and the first driving unit 171 and the second driving unit 172 are completely independent of the third driving unit 173. In Addition, since the main decoupling element 1761 and the coupling source causing the coupling relationship, i.e., the third driving unit 173, rotate coaxially, the main decoupling element 1761 and the third driving unit 173 move at the same angular velocity, and the main decoupling element 1761 and the coupling source third driving unit 173 move synchronously, no main operation setting is required to give a signal to control the decoupling member, the movement of the decoupling member runs in synchronization with the movement of the coupling source, the decoupling member synchronizes the third driving unit for decoupling without any delay, and the length variation of the first pair of cables and the second pair of cables on one side of the end-effector 150 caused by the third driving unit 173 of the coupling source can be completely and precisely mapped to the length variation of the first pair of cables and the second pair of cables on the decoupling member 176, so that the decoupling member 176 can completely and precisely release the coupling relationship between the third pair of cables and the first pair of cables and the second pair of cables, the so-called precise decoupling refers to how much the third driving unit rotates, how much distance is moved from the slave decoupling element, the relationship between the two is determined, and the above radius ratios are given. In Addition, since the slave decoupling element 176 is always driven by the main decoupling element 1761 to move to the corresponding position, instead of being driven by the first pair of cables or the second pair of cables, the first pair of cables and the second pair of cables are substantially unstressed from the slave decoupling element during the entire decoupling process, so that the tension of the first pair of cables and the second pair of cables during the decoupling process is substantially unchanged, thereby increasing the service life of the first pair of cables and the second pair of cables and the accuracy of controlling the end effector 150.

Figure 10A:
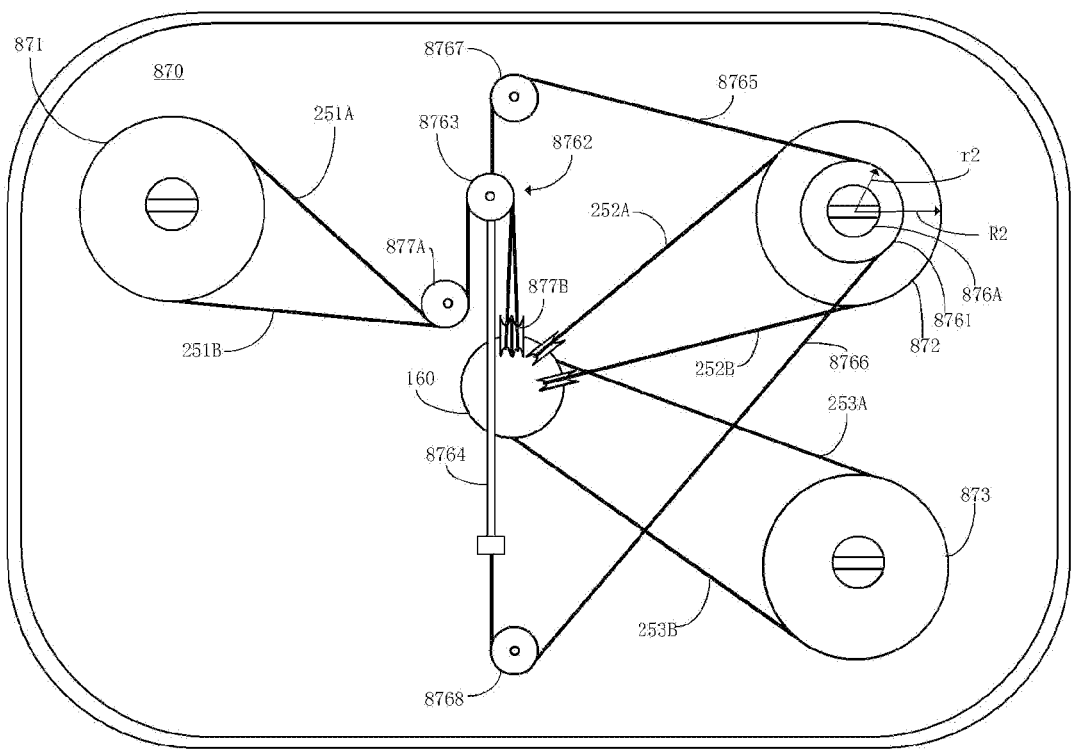
FIG. 10A is a schematic view of a driving apparatus shown in FIG. 8A.
Figure 10B:
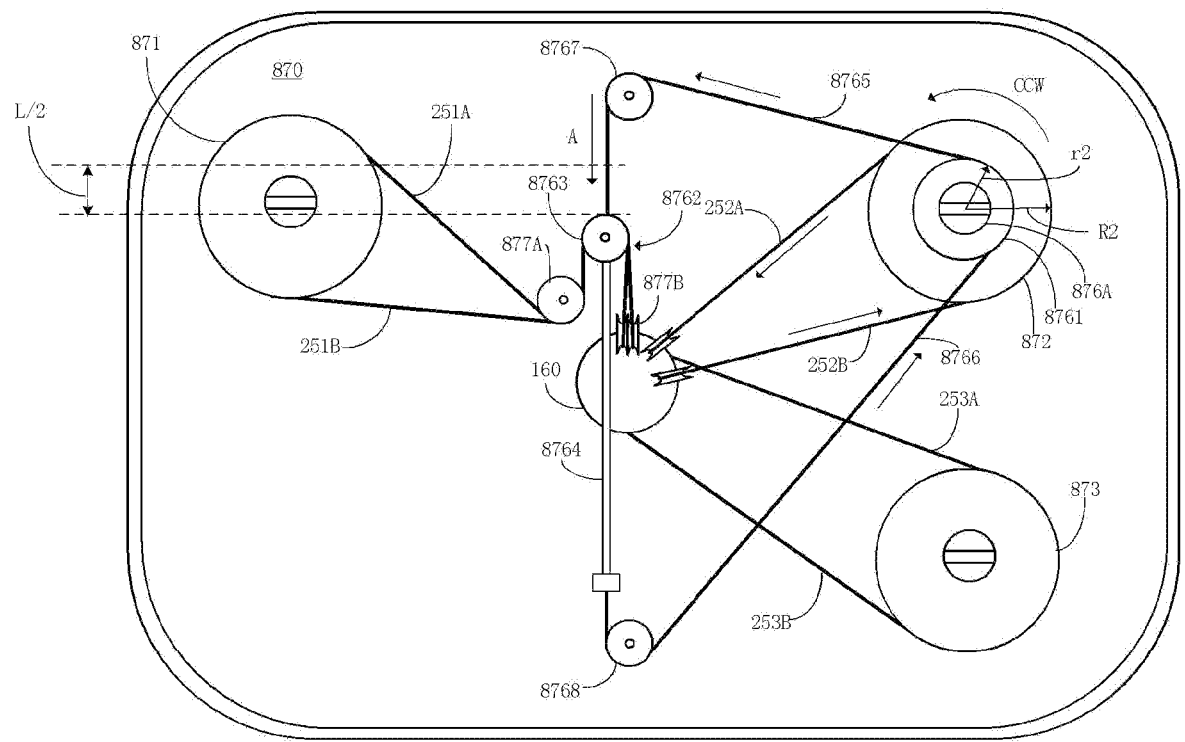
FIG. 10B is a schematic view of a decoupling process of the driving apparatus shown in FIG. 10A.

One embodiment of the present disclosure is suitable for driving the driving apparatus as shown in FIGS. 10A and 10B of the end effector 250 shown in FIGS. 8A-8E, and the driving apparatus 870 includes a first driving unit 871 for driving the end effector 250 to yaw, a second driving unit 872 for driving the end effector 250 to pitch, and a third driving unit 873 for driving the end effector 250 to rotate. The first driving cables 251A and 251B of the first pair of cables used to manipulate the yaw movement of the end effector 250 are wound on the first driving unit 871 in an opposite manner, the second driving cables 252A and the third driving cables 252B of the second pair of cables for manipulating the pitch movement of the end effector 250 are wound on the second driving unit 872 in an opposite manner, and the third driving unit 873 is wound with a fourth driving electric cable 253A for driving the rotation of the long axis 160. As can be seen from the above with respect to FIGS. 8A-8E, there is also a coupling relationship between the second pair of cables and the first pair of cables, and the driving apparatus 870 further comprises a decoupling member for release the coupling relationship between the second pair of cables and the first pair of cables.

The decoupling member includes a main decoupling element 8761 and a slave decoupling element 8762, the main decoupling element 8761 and the second driving unit 872 Are disposed on the same rotating shaft 872A, the main decoupling element 8761 and the second driving unit 872 move at the same angular velocity with the rotating shaft 872A, and the main decoupling element 8761 receives the same driving power as the second driving unit 872 and drives the slave decoupling element 8762 to release the above coupling relationship. The slave decoupling element 8762 includes a guiding portion 8763 and a carriage 8764, the main decoupling element 8761 is connected to one end of the carriage 8764 by a first decoupling cable 8765 and connected to the other end of the carriage 8764 by a second decoupling cable 8766, the driving apparatus 870 drives the slave decoupling element 8763 to move linearly through the first decoupling cable 8765 and the second decoupling cable 8766.

The driving apparatus further comprises a first guiding pulley 877A, a second guiding pulley 877B, a third guiding pulley 8767, and a fourth guiding pulley 8768. The first pair of cables is redirected by the first guiding pulley 877A and then passes through the guiding portion 8763 and finally enters the long shaft 160 through the second guiding pulley 877B. In other words, a part of the first pair of cables in contact with the guiding portion 8763 is between a part of the first pair of cables in contact with the first guiding pulley 877A and with the end effector 250, and a moving direction of the carriage 8764 is parallel to a portion of the first pair of cables between the first guiding pulley 877A and the guiding portion 8763. The first decoupling cable 8765 is redirected by the third guiding pulley 8767 and then connected to the carriage 8764, the second decoupling cable 8766 is redirected by the fourth guiding pulley 8768 and then connected to the carriage 8764, and the portion of the first decoupling cable 8765 between the third guiding pulley 8767 and the carriage 8764 is parallel to the direction of motion of the carriage 8764. The portion of the second decoupling cable 8766 between the fourth guiding pulley 8768 and the carriage 8764 is also parallel to the direction of motion of the carriage 8764. Therefore, in the decoupling process, the movement speed of the carriage 8764 is proportional to the rotational linear speed of the main decoupling element 8761. It can be understood that in some other embodiments, the main decoupling element may also be connected to the slave decoupling member through a gear or a cam as in the previous several embodiments, and specifically refer to the above embodiments of gear connection or cam connection, which will not be repeated here.

The portion of the first driving cable 251A and the second driving cable 251B between the first guiding pulley 877A and the guide portion 8763 are parallel to the movement direction of the carriage 8764, and portion of the first driving cable 251A and the second driving cable 251B between the guiding portion 8763 and the second guiding pulley 877B are parallel to the movement direction of the carriage 8764. Therefore, in the decoupling process, the speed of the change in length of the first driving cable 251A and the second driving cable 251B in the driving apparatus is proportional to the speed of the linear motion of the carriage 8764. As described above, the movement speed of the carriage 8764 is proportional to the rotational linear speed of the main decoupling element 8761 and the rotational linear speed of the second driving unit 872, so that the speed of the change in length of the first driving cable 251A and the second driving cable 251B in the driving apparatus is proportional to the rotational linear speed of main decoupling element 8761 and the rotational linear speed of the second driving unit 872, making the decoupling process more precise and controllable. In this embodiment, the change speed of the length of the first driving cable 251A and the second driving cable 251B in the driving apparatus is twice as the rotational line speed of the main decoupling element 8761.

The decoupling process of the decoupling member is shown in FIG. 10B, when the second driving unit 872 rotates counterclockwise (the first direction), the second driving unit pulls the fourth driving cable 252B and simultaneously releases the third driving cable 252A, since the main decoupling element 8761 and the second driving unit 872 rotate at the same angular velocity, so that the main decoupling element 8761 simultaneously pulls the second decoupling cable 8766 and releases the first decoupling cable 8765, causing the slave decoupling element 8762 to move in the A direction, thereby the length of the first pair of cables in the driving apparatus 870 is reduced, and the length of the first pair of cables on the end effector 250 is increased. When the movement distance of the driving unit 8762 in the A direction is L/2, and similar to the previous several embodiments, the length of both the first driving cable 251A and the second driving cable 251B in the driving apparatus 870 is reduced by L respectively.

As shown in FIG. 8D and FIG. 10B, when the radius of the third pulley 443 and the radius of the fourth pulley 444 are both r1, the groove bottom radius of annular groove 421A of the pitch pulley 421A for accommodating the second pair of cables is R1, the radius of the main decoupling element 8761 is r2, and the radius of the second driving unit 872 is R2, and in order to achieve accurate decoupling, the radii r1 of the third pulley 443 and the fourth pulley 444, the groove bottom radius R1 of annular groove 421A, the radius r2 of the main decoupling element 8761, and the radius R2 of the second driving unit 872 satisfy the following relationship:

$$\frac{R2}{r2} = 2\frac{R1}{r1}$$

The specific derivation process is the same as the embodiment shown in FIG. 7A, and details are not described herein again. In other embodiments, the number of the guiding portions of the slave decoupling element can be other and the relationship between the ratio of the third driving unit to the radius of the main decoupling element and the ratio of the radius of the pitch pulley to the radius of the second pair of pulleys also changes, for example, the slave decoupling element can have N guiding pulley and the radius of the third driving unit to the radius of the main decoupling element is 2*N times the ratio of the radius of the pitch pulley to the radius of the second pair of pulleys, that is:

$$\frac{R2}{r2} = 2*N\frac{R1}{r1}.$$

However, the increase in the number of guiding portions of the slave decoupling element, causing a corresponding increase in the size of the slave decoupling element. Optionally, in the above embodiment, one guiding portion is used from the slave decoupling element, the guiding portion is a pulley passing through the first driving cable on the slave decoupling element.

Therefore, the decoupling member in the driving apparatus 870 provides the variable quantity of the length of the first driving cable 251A and the second driving cable 251B on one side of the end effector 250 required by the pitch movement of the end effector 250, thereby releasing the coupling relationship between the third pair of cables and each of the first pair of cables and the second pair of cables, and the movement of the third pair of cables is no longer limited by the first driving cable and the second driving cable, so that the end effector 250 can perform the pitch movement smoothly and the end effector 250 can achieve the pitch movement shown in FIGS. 8D, 8E.

When the main decoupling element 8761 and the second driving unit 872 rotate clockwise coaxially, the change in the driving cable is opposite to the counter-clockwise rotation, and at this time, the second driving unit 872 pulls the third driving cable 252A and releases the fourth driving cable 252B, and the main decoupling element 8761 pulls the first decoupling cable 8765 and releases the second decoupling cable 8766 to drive the slave decoupling element 8762 to move in the opposite direction from the A direction, thereby increasing the length of the first driving cable 251A and 251B within the driving apparatus, which is just equal to the reduction amount of the first driving cable 251A and the second driving cable 251B on the second pair of pulleys of the end effector 250. The first driving cable 251A and the second driving cable 251B do not slacken on the end effector 250, so that the end effector 250 can perform the pitch movement smoothly in the opposite direction as shown in FIG. 8D.

The above embodiments only express several embodiments of the present disclosure, which are described in a more specific and detailed manner, but they should not be constructed as limiting the scope of the present disclosure. It should be noted that, for a person of ordinary skill in the art, several variations and improvements can be made without departing from the conception of the present disclosure, and these fall within the protection scope of the present disclosure. Therefore, the scope of protection of the present disclosure shall be subject to the appended claims.

What is claimed is:

1. A surgical instrument, comprising:
an end effector, comprising a first frame, a second frame, and an executive component, the second frame being rotatably connected to the first frame, and the executive component being rotatably connected to the second frame;
a driving cable, comprising a first pair of cables and a second pair of cables, a distal end of the first pair of cables being arranged at the executive component, a distal end of the second pair of cables being arranged on the second frame, a first pair of pulleys and a second pair of pulleys for guiding the first pair of cables and the second pair of cables being arranged on the first frame, and the second pair of pulleys being disposed between the first pair of pulleys and the executive component; and
a driving apparatus, configured to drive the executive component to rotate relative to the second frame through the first pair of cables whereby the end effector performs a yaw movement, and further configured to drive the second frame to rotate relative to the first frame through the second pair of cables whereby the end effector performs a pitch movement;
wherein the driving apparatus comprises a driving unit and a decoupling member, one end of the second pair of cables is connected to the driving unit, the driving unit drives the end effector to perform the pitch movement through the second pair of cables;
the decoupling member comprises a main decoupling element and a slave decoupling element, the main decoupling element and the slave decoupling element are arranged coaxially, the main decoupling element is configured for coaxially rotating with the driving unit and driving the slave decoupling element to move so as to increase or reduce a length of the first pair of cables in the driving apparatus, so that the driving unit drives the end effector to perform the pitch movement.

2. The surgical instrument of claim 1, wherein the first pair of cables comprises a first driving cable and a second driving cable, each of the first driving cable and the second driving cable is connected to one side of the executive component; the driving apparatus causes the end effector to perform the yaw movement by pulling one of the first driving cable and the second driving cable, and releasing the other one of the first driving cable and the second driving cable.

3. The surgical instrument of claim 2, wherein the second pair of cables comprises a third driving cable and a fourth driving cable, each of the third driving cable and the fourth driving cable is connected to one side of the second frame; the driving apparatus causes the end effector to perform the pitch movement by pulling one of the third driving cable and the fourth driving cable, and releasing the other one of the third driving cable and the fourth driving cable.

4. The surgical instrument of claim 3, wherein a winding manner of the first driving cable around the first pair of pulleys and the second pair of pulleys is the same as that of the second driving cable around the first pair of pulleys and the second pair of pulleys.

5. The surgical instrument of claim 4, wherein the first pair of pulleys comprises a first pulley and a second pulley connected in sequence to a shaft, the driving apparatus releases the third driving cable and pulls the fourth driving cable so as to increase a wrapping length of the first driving cable on the first pulley and a wrapping length of the second driving cable on the second pulley simultaneously, whereby the second frame rotates relative to the first frame.

6. The surgical instrument of claim 5, wherein the main decoupling element drives the slave decoupling element to move linearly to increase or decrease the length of the first pair of cables in the driving apparatus.

7. The surgical instrument of claim 6, wherein the first driving cable and the second driving cable cooperatively drive the end effector to perform the yaw movement, the driving unit rotates and pulls one of the third driving cable and fourth driving cable, and releases the other one cable such that lengths of the first driving cable and the second driving cable on the end effector increase or decrease simultaneously.

8. The surgical instrument of claim 7, wherein the driving unit and the main decoupling element are configured to rotate in a first direction, the driving unit releases the third driving cable and pulls the fourth driving cable to increase the lengths of the first driving cable and the second driving cable on the end effector, and the slave decoupling element moves when driven by the main decoupling element to reduce the lengths of the first driving cable and the second driving cable in the driving apparatus.

9. The surgical instrument of claim 8, wherein the slave decoupling element comprises a carriage and a guiding portion, the guiding portion is mounted at one end of the carriage, the first pair of cables extends to the end effector after the first pair of cables is guided by the guiding portion, and the main decoupling element is connected to the carriage and drives the carriage to move so as to change the length of the first pair of cables in the driving apparatus.

10. The surgical instrument of claim 9, wherein the slave decoupling element further comprises a first decoupling cable and a second decoupling cable, the main decoupling element is connected with the carriage through the first decoupling cable and the second decoupling cable, and the main decoupling element is configured for driving the carriage to move through the first decoupling cable and the second decoupling cable so as to change the length of the first pair of cables in the driving apparatus.

11. The surgical instrument of claim 10, wherein the main decoupling element rotates in the first direction to release the first decoupling cable and pull the second decoupling cable such that the carriage moves in a direction for reducing the lengths of the first driving cable and the second driving cable in the driving apparatus.

12. The surgical instrument of claim 9, wherein the driving apparatus further comprises a first guiding pulley, a part of the first pair of cables in contact with the guiding portion is between a part of the first pair of cables in contact with the first guiding pulley and with the end effector, and a moving direction of the carriage is parallel to a portion of the first pair of cables between the first guiding pulley and the guiding portion.

13. The surgical instrument of claim 12, wherein both a radius of the first pulley and a radius of the second pulley is r1, a radius of the main decoupling element is r2, a radius of the driving unit is R2, a radius of the annular groove is R1, and the r1, r2, R1, and R2 satisfy the following relationship:

$$\frac{R2}{r2} = 2*N\frac{R1}{r1}$$

wherein, N is a number of the guiding portion.

14. The surgical instrument of claim 13, wherein a length variation of the first driving cable in the driving apparatus is twice as much as a moving distance of the slave decoupling element.

15. The surgical instrument of claim 12, wherein a movement speed of the carriage is proportional to a rotational linear speed of the main decoupling element.

16. The surgical instrument of claim 7, wherein the first frame has a first hole and a second hole, the first hole is configured for the first driving cable to pass through, the second hole is configured for the second driving cable to pass through, the first hole and the second hole are located on a same side of a plane containing an axis defined by the first pair of pulleys and an axis defined by the second pair of pulleys.

17. The surgical instrument of claim 16, wherein the executive component further comprises a first insulation member, a second insulation member, a third insulation member, and an electric cable for supplying power to the executive component, a proximal end of the executive component is connected to a distal end of the electric cable in the first insulation member, the second insulation member is connected to a distal end of the first insulation member, an end portion of the executive component is fixed in the second insulation member, and the distal end of the electric cable is accommodated in the third insulation member and extends into the first insulation member to be connected to a proximal end of the executive component.

18. The surgical instrument of claim 17, wherein the second pulley and the fourth pulley have a guiding portion configured for guiding the electric cable.

19. A surgical robot, comprising a main operation console and a slave operation device, the slave operation device performing a corresponding operation according to an instruction from the main operation console, the slave operation device comprising a robotic arm and a surgical instrument, the surgical instrument being mounted on the robotic arm, and the robotic arm being configured for manipulating the surgical instrument to move, the surgical instrument comprising:

an end effector, comprising a first frame, a second frame, and an executive component, the second frame being rotatably connected to the first frame, and the executive component being rotatably connected to the second frame;

a driving cable, comprising a first pair of cables and a second pair of cables, a distal end of the first pair of cables being arranged at the executive component, a distal end of the second pair of cables being arranged on the second frame, a first pair of pulleys and a second pair of pulleys for guiding the first pair of cables and the second pair of cables being arranged on the first frame, and the second pair of pulleys being disposed between the first pair of pulleys and the executive component; and a driving apparatus, configured to drive the executive component to rotate relative to the second frame through the first pair of cables whereby the end effector performs a yaw movement, and further configured to drive the second frame to rotate relative to the first frame through the second pair of cables whereby the end effector performs a pitch movement;

wherein the driving apparatus comprises a driving unit and a decoupling member, one end of the second pair of cables is connected to the driving unit, the driving unit drives the end effector to perform the pitch movement through the second pair of cables;

the decoupling member comprises a main decoupling element and a slave decoupling element, the main decoupling element and the slave decoupling element are arranged coaxially, the main decoupling element is configured for coaxially rotating with the driving unit and driving the slave decoupling element to move so as to increase or reduce a length of the first pair of cables in the driving apparatus, so that the driving unit drives the end effector to perform the pitch movement.

* * * * *